US012252502B2

(12) United States Patent
Jeon et al.

(10) Patent No.: US 12,252,502 B2
(45) Date of Patent: Mar. 18, 2025

(54) L-GLUFOSINATE INTERMEDIATE AND L-GLUFOSINATE PREPARATION METHOD

(71) Applicant: CJ CheilJedang Corporation, Seoul (KR)

(72) Inventors: Jinwoo Jeon, Seoul (KR); Joo Young Lee, Seoul (KR); Changsuk Lee, Seoul (KR); Hyunjin Kim, Seoul (KR); Jun Ok Moon, Seoul (KR); In Seok Oh, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 807 days.

(21) Appl. No.: 17/311,743

(22) PCT Filed: Nov. 29, 2019

(86) PCT No.: PCT/KR2019/016788
§ 371 (c)(1),
(2) Date: Jun. 8, 2021

(87) PCT Pub. No.: WO2020/145513
PCT Pub. Date: Jul. 16, 2020

(65) Prior Publication Data
US 2022/0024955 A1 Jan. 27, 2022

(30) Foreign Application Priority Data

| Jan. 11, 2019 | (KR) | 10-2019-0004164 |
| Jan. 15, 2019 | (KR) | 10-2019-0005282 |
| Jan. 15, 2019 | (KR) | 10-2019-0005283 |
| Jan. 15, 2019 | (KR) | 10-2019-0005404 |
| Jan. 15, 2019 | (KR) | 10-2019-0005405 |

(51) Int. Cl.
*C07F 9/54* (2006.01)
*C07C 231/12* (2006.01)
*C07D 307/33* (2006.01)
*C07F 7/18* (2006.01)
*C07F 9/30* (2006.01)
*C07F 9/32* (2006.01)

(52) U.S. Cl.
CPC .......... *C07F 9/5428* (2013.01); *C07C 231/12* (2013.01); *C07D 307/33* (2013.01); *C07F 7/1896* (2013.01); *C07F 9/301* (2013.01); *C07F 9/3205* (2013.01); *C07B 2200/07* (2013.01)

(58) Field of Classification Search
CPC ...... C07F 9/5428; C07F 7/1896; C07F 9/301; C07F 9/3205; C07C 231/12; C07C 231/00; C07C 235/12; C07D 307/33; C07B 2200/07; B01J 27/10; B01J 27/24
USPC ........................................................ 549/321
See application file for complete search history.

(56) References Cited

U.S. PATENT DOCUMENTS 5,442,088 A   8/1995 Hoffmann et al.
2002/0146783 A1  10/2002 Maier et al.

FOREIGN PATENT DOCUMENTS

| CN | 1370836 | 9/2002 |
| CN | 101230000 | 7/2008 |
| CN | 101550100 | 10/2009 |
| CN | 106045947 | 10/2016 |
| CN | 106083922 | 11/2016 |
| CN | 106518695 | 3/2017 |
| KR | 10-2002-0067623 | 8/2002 |
| KR | 10-2013-0006464 | 1/2013 |
| KR | 10-2014-0116010 | 10/2014 |
| KR | 10-2018-0117154 | 10/2018 |
| PL | 208845 | 6/2011 |
| RU | 2275376 | 4/2006 |
| WO | 2017/151573 | 9/2017 |
| WO | 2018-019867 | 2/2018 |
| WO | 2020-145513 | 7/2020 |

OTHER PUBLICATIONS

Zhou Zhong-qiang et al. "Synthesis of S-a-(methyloxycarbonyl) amino-g-butyrolactone" Chinese Journal of Pesticides vol. 45, No. 1 (Jan. 2006). pp. 22-23, 30. Only abstract translated.
Peter G.M.Wuts, "Greene's Protective Groups in Organic Synthesis", Fourth Edition, 2007, p. 706, 773.
J.-H. Lee et al., "In Vitro Characterization of a Heterologously Expressed Nomibosomal Peptide Synthetase Involved in Phosphinothricin Tripeptide Biosynthesis", Biochemistry, 2009, vol. 48, No. 23, pp. 5054-5056; doi: 10.1021/bi900164d.
G. Knaup et al., "O-Acetyl-L-homoserine: A versatile synthon for the synthesis of L-homoserine peptides and 3-amino-2-pyrrolidinones", Peptides for the New Millennium, Kluwer Academic publishers, 1999, vol. 16, pp. 66-67; doi: 10.1007/0-306-46881-6_2.
KIPO, PCT Search Report & Written Opinion of PCT/KR2019/016788 dated Mar. 16, 2020.
Michael G. Hoffmann et al., "A Novel and Convenient Route to L-Homoserine Lactones and L-Phosphinothricin From L-Aspartrj Acid", Tetrahedron Letters, vol. 33, No. 19, 1992, pp. 2669-2672.
Jin-Hee Lee et al., "In Vitro Characterization of a Heterologously Expressed Nonribosomal Peptide Synthetase Involved in Phosphinothricin Tripeptide Biosynthesis", Biochemistry, 2009, 48, 5054-5056.
Guenter Knaup et al., "O-Acetyl-L-homoserine: A versatile synthon for the synthesis of L-homoserine peptides and 3-amino-2-pyrrolidinones", Peptides for the New Millennium, 1999, 66-67.
Suneel P. Singh et al., "A Microwave-Assisted Synthesis of (S)-N-Protected Homoserine γ-Lactones from L-Aspartic Acid", J. Org. Chem. 2011, 76, 6825-6831.

(Continued)

Primary Examiner — Taylor V Oh
(74) Attorney, Agent, or Firm — LEX IP MEISTER, PLLC

(57) ABSTRACT

Provided are L-glufosinate intermediate preparation method or L-glufosinate preparation method, the method, for preparing L-glufosinate intermediate or L-glufosinate from an L-homoserine derivative, comprising a step of preparing a compound of Chemical Formula 2 from a compound of Chemical Formula 1.

21 Claims, No Drawings

(56) References Cited

OTHER PUBLICATIONS

Walker, D. M. et al. "Design and synthesis of γ-oxygenated phosphinothricins as inhibitors of glutamine synthetase", Journal of the Chemical Society. Perkin Transactions I. 1990, vol. 3, pp. 659-666, 1990.
Walker, D. M. et al., "Synthesis of D,L-γ-hydroxyphosphinothricin, a potent new inhibitor of glutamine synthetase", Journal of the Chemical Society. Chemical Communications. 1987. vol. 22, pp. 1710-1711, 1987.
Theodora W Greene et al., "Protection for the Amino Group", Protective Groups in Organic Synthesis, 3rd Edition, John Wiley & Sons, Inc, New York, pp. 494-653, XP009527465, Apr. 9, 1999.
MYIPO, Office Action of the corresponding MY Patent Application No. PI2021003431, dated Sep. 28, 2022.
EPO, Extended European search report of the corresponding EP Patent Application No. 19908870.9, dated Nov. 24, 2022.
Australian Patent Office, Office Action of AU 2019421447 dated Mar. 4, 2022.

L-GLUFOSINATE INTERMEDIATE AND L-GLUFOSINATE PREPARATION METHOD

TECHNICAL FIELD

The present invention relates to a method for preparing L-glufosinate intermediate.

BACKGROUND ART

Glufosinate is widely used as a broad-spectrum herbicide having penetrability, and it is known that the properties of the permeable herbicide glufosinate are the effects caused by an L-isomer of glufosinate. Thereby, various methods for preparing the L-isomer of glufosinate have been studied. For example, a method of preparing a L-isomer of glufosinate by selectively separating the L-isomer from a racemic mixture of D-isomer and L-isomer was used. Such a method has problems that the yield of L-isomer is reduced by a half or less, unwanted D-isomers are produced as excessive by-products, a resolving agent, a resolving device, and the like are required for the separation of the L-isomer, and thus, the process is complicated.

Therefore, there is a need to develop a method of preparing an L-isomer of glufosinate with high optical purity in a simple manner and in a high yield.

DETAILED DESCRIPTION OF THE INVENTION

Technical Problem

An object of the present application is to provide a method of preparing glufosinate intermediate for the preparation of L-glufosinate with high optical purity, and L-glufosinate in a simple manner and in a high yield.

Technical Solution

In one aspect, there is provided a method for preparing L-glufosinate intermediate from an L-homoserine derivative, the method comprising a step of preparing a compound of the following Chemical Formula 2 from a compound of the following Chemical Formula 1.

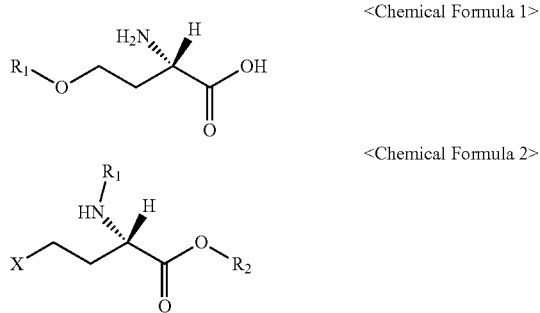

<Chemical Formula 1>

<Chemical Formula 2> where in the above formulas, $R_1$ is $R_a$—(C=O)—, where $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_d$), where $R_b$, $R_c$ and $R_d$ independently of one another are a substituted or unsubstituted alkyl group having 1 to 6 carbon atoms or a substituted or unsubstituted aryl group having 6 to 20 carbon atoms, X is halogen, and substituents of the alkyl group, alkenyl group, alkynyl group, cycloalkyl group, aryl group, and heteroaryl group independently of one another are at least one selected from halogen, a carboxyl group (—COOH), an amino group (—NH$_2$), a nitro group (—NO$_2$), a cyano group (—CN), an alkyl group having 1 to 6 carbon atoms, an aryl group having 6 to 10 carbon atoms, and a cycloalkyl group having 3 to 10 carbon atoms.

In another aspect, there is provided a method for preparing L-glufosinate from an L-homoserine derivative, the method comprising a step of preparing the compound of Chemical Formula 2 from the compound of Chemical Formula 1.

Advantageous Effects

According to one embodiment, since the present invention allows simple production of L-glufosinate with high optical purity by using an L-homoserine derivative as a starting material and having a synthetic route including a new intermediate compound.

In addition, by using the L-homoserine derivative as a starting material, the terminal group in the L-homoserine derivative can transfer to the amine group without the need to introduce a separate protecting group, thereby allowing production of an intermediate compound containing an amine protecting group. Thus, charging of an additional compound is not required for introduction of a separate protecting group. Therefore, the process is simple and the production of by-products can be reduced.

Detailed Description of the Embodiments

Hereinafter, a method for preparing L-glufosinate intermediate or L-glufosinate according to one embodiment will be described in more detail.

The inventive concept of the present application described below can be modified in various forms and can have various embodiments, and thus, specific embodiments will be illustrated and described in detail. However, the embodiments are not intended to limit the inventive concept of the present application, but it should be understood that the invention includes all modifications, equivalents, and replacements belonging to the technical scope of the inventive concept of the present application.

As used herein, terms such as first, second, third, fourth, and the like may be used to describe various components, but the components should not be limited by the terms. The terms are used only to discriminate one constituent element from another component.

The term 'L-glufosinate' as used herein is an L-isomer of glufosinate. The term 'D-glufosinate' as used herein is a D-isomer of glufosinate.

The term '% enantiomeric excess (% ee)' means the enantiomeric purity of a sample, that is, the percentage of one enantiomer that exceeds the other enantiomer in the sample. For example, the enantiomeric excess of L-glufosinate is the percentage of L-glufosinate that exceeds D-glufosinate in the glufosinate. For example, the enantiomeric excess of L-glufosinate is represented by Equation 1 below.

Enantiomeric excess of L-glufosinate=[(Content of L-glufosinate−Content of D-glufosinate)/(Content of L-glufosinate+Content of D-glufosinate)]×100   <Equation 1>

The method for preparing L-glufosinate intermediate of the present invention can use an L-homoserine derivative as a starting material. That is, the method may include a step (step a) of preparing a compound of the following Chemical Formula 2 from a compound of the following Chemical Formula 1.

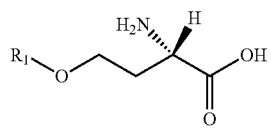
<Chemical Formula 1>

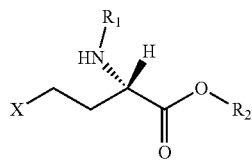
<Chemical Formula 2> where in the above formulas, $R_1$ is $R_a$—(C=O)—, where $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_d$), where $R_b$, $R_c$ and $R_d$ independently of one another are a substituted or unsubstituted alkyl group having 1 to 6 carbon atoms or a substituted or unsubstituted aryl group having 6 to 20 carbon atoms, X is halogen, and substituents of the alkyl group, alkenyl group, alkynyl group, cycloalkyl group, aryl group, and heteroaryl group independently of one another are at least one selected from halogen, a carboxyl group (—COOH), an amino group (—NH$_2$), a nitro group (—NO$_2$), a cyano group (—CN), an alkyl group having 1 to 6 carbon atoms, an aryl group having 6 to 10 carbon atoms, and a cycloalkyl group having 3 to 10 carbon atoms.

The step (step a) of preparing the compound of Chemical Formula 2 from the compound of Chemical Formula 1 may include a step (step b) of preparing a compound of the following Chemical Formula 3 by reacting the compound of Chemical Formula 1 with a first base catalyst.

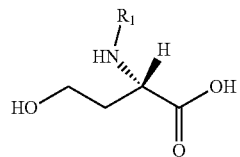
<Chemical Formula 3> where in the Chemical Formula 3, $R_1$ is as defined above.

The step (step a) of preparing the compound of Chemical Formula 2 from the compound of Chemical Formula 1 may include a step (step c) of preparing a compound of the following Chemical Formula 4 by reacting the compound of Chemical Formula 3 with a first acid catalyst after the step b.

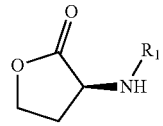
<Chemical Formula 4>

$R_1$ is as defined above in the Chemical Formula 3

Then, the step (step a) of preparing the compound of Chemical Formula 2 from the compound of Chemical Formula 1 may include a step (step d) of preparing the compound of Chemical Formula 2 by reacting the compound of Chemical Formula 4 with a halogenating agent and at least one $R_2$—OH after the step c.

According to the present invention, by using an L-homoserine derivative as a starting material, and going through a synthetic route for obtaining an intermediate compound containing an amine protecting group, an intermediate compound having a lactone ring, and an intermediate compound as a halogenated compound, it is possible to prepare L-glufosinate with high optical purity in a simple manner and in high yield.

More specifically, an L-homoserine derivative represented by the following Chemical Formula 1 can be reacted with a first base catalyst to prepare a first intermediate compound represented by the following Chemical Formula 3.

In the L-homoserine derivative represented by Chemical Formula 1, the $R_a$(C=O)-functional group represented by $R_1$ can be bonded to nitrogen in the first intermediate compound represented by Chemical Formula 2 by a functional group transfer reaction under the first base catalyst. Therefore, in the first intermediate compound represented by Chemical Formula 2, since $R_1$ can act as a protecting group of an amine, the process is simple and economical because an additional compound for introducing a separate protecting group is not required. Further, the production of by-products can be reduced.

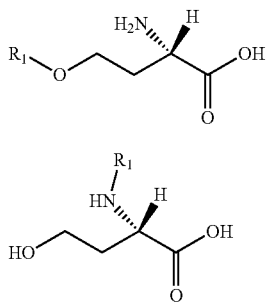

<Chemical Formula 1>

<Chemical Formula 3>

In the L-homoserine compound represented by Chemical Formula 1 and the first intermediate compound represented by Chemical Formula 2, for example, $R^1$ may be acetyl or succinyl. Since the L-homoserine compound represented by Chemical Formula 1 and the first intermediate compound represented by Chemical Formula 3 have such functional groups, L-glufosinate having improved optical purity may be more easily prepared.

The L-homoserine derivative represented by Chemical Formula 1 can be prepared, for example, from a fermentation liquid containing an L-homoserine derivative. Therefore, it is possible to efficiently prepare L-glufosinate by using the L-homoserine derivative represented by Chemical Formula 1 that is produced in the fermentation process.

As used herein, the term 'fermentation liquid containing an L-homoserine derivative' may be a fermentation liquid containing an L-homoserine derivative that is produced from a fermentation process. The fermentation liquid may be a fermentation liquid obtained by culturing microorganisms in a medium containing sugar, or alternatively, may be a fermentation liquid which is obtained by enzymatically converting a fermentation liquid obtained by culturing microorganisms. For example, the fermentation liquid containing an L-homoserine derivative may be a fermentation liquid in which microorganisms are cultured in a medium containing sugar to directly produce an L-homoserine derivative, or a fermentation liquid containing an L-homoserine derivative which is obtained by enzymatically converting an amino acid produced by culturing a microorganism in a medium containing sugar. The type of microorganisms used in the preparation of the fermentation liquid containing the L-homoserine derivative is not particularly limited, and any microorganism capable of producing an L-homoserine derivatives by direct fermentation or enzymatic conversion in the technical field can be used.

The L-homoserine derivative includes, for example, O-acetyl-L-homoserine, 0-succinyl L-homoserine, but are not necessarily limited thereto, and are obtained during fermentation, and any derivative in which a substituent group is linked to a terminal oxygen of L-homoserine can be used in the technical field.

The fermentation liquid containing an L-homoserine derivative may be, for example, a fermentation liquid obtained by fermenting a medium containing O-succinyl-L-homoserine-producing strain CJM-BTJ/pCJ-MetA-CL (accession number: KCCM-10872) or O-acetyl-L-homoserine-producing strain CJM-BTJA/pCJ-MetX-CL (accession number: KCCM-10873) disclosed in Example 2 of Korean Unexamined Patent Publication No. 10-2014-0116010.

The first base catalyst may be at least one selected from the group consisting of $NH_3$, KOH, NaOH, $CaSO_4$, LiOH, NaH, KH, $NaOCH_3$, $NaOCH_2CH_3$, $NaOC(CH_3)_3$, KOC $(CH_3)_3$, $K_2CO_3$, $Na_2CO_3$, 1,8-diazabicyclo[5.4.0]undeca-7-ene (DBU), 1,5-diazabicyclo[4.3.0]nona-5-ene (DBN), tri ($C_1$-$C_4$ alkyl)amine, pyridine and n-butyllithium, without being limited thereto. The first base catalyst may be particularly sodium hydroxide.

The content of the first base catalyst may be, for example, 0.1 to 100 parts by weight, 0.1 to 50 parts by weight, 0.1 to 40 parts by weight, 0.1 to 30 parts by weight, 0.1 to 20 parts by weight, 0.1 to 10 parts by weight, 0.1 to 5 parts by weight, or 0.1 to 2 parts by weight based on 100 parts by weight of the L-homoserine derivative represented by Chemical Formula 1. When the content of the first base catalyst is too low, it may have a slight effect on the reaction rate, and when the content of the first base catalyst is too large, by-products may increase.

The step of preparing the first intermediate compound may be carried out under a solvent. The solvent may be water or an organic solvent. The organic solvent may be, for example, alcohol, toluene, benzene, tetrahydrofuran, chloroform, dichloromethane, acetonitrile, or the like. The alcohol may be, for example, methanol, ethanol, propanol, butanol, pentanol, or the like, without being limiting thereto.

When the first base catalyst is used and the solvent is water, the pH of the aqueous solution containing water may be 9 to 14, 10 to 14, or 12 to 14. That is, in the step of preparing the first intermediate compound, the reaction solution may be a basic aqueous solution with a pH of 9 to 14. As the reaction solution has a pH in this range, the first intermediate compound can be more easily prepared.

In the step of preparing the first intermediate compound, the functional group transfer reaction may be carried out at a temperature of, for example, 20 to 150° C., 20 to 100° C., 20 to 90° C., 30 to 70° C., or 40 to 60° C. In the step of preparing the first intermediate compound, the functional group transfer reaction may be carried out, for example, for 0.1 to 20 hours, 0.1 to 15 hours, 0.5 to 10 hours, 1 to 9 hours, 2 to 8 hours, 3 to 7 hours, or 4 to 6 hours. As a functional group transfer reaction is carried out within the above temperature range and time range, the first intermediate compound may be more easily prepared.

In the step of preparing the first intermediate compound, the yield of the first intermediate compound may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the step of preparing the first intermediate compound, the enantiomeric excess of the first intermediate compound may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more.

Next, the first intermediate compound represented by Chemical Formula 3 can be reacted with the first acid catalyst to prepare a second intermediate compound represented by Chemical Formula 4. That is, the first intermediate compound represented by Chemical Formula 3 can be lactonized using a first acid catalyst to prepare a lactone compound represented by the following Chemical Formula 4. For example, the first intermediate compound represented by Chemical Formula 3 may form a lactone ring by the first acid catalyst.

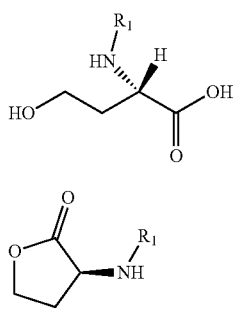

<Chemical Formula 3>

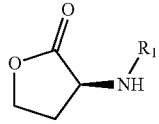

<Chemical Formula 4>

In the first intermediate compound represented by Chemical; Formula 3 and the second intermediate compound represented by Chemical Formula 4, for example, $R_1$ may be acetyl or succinyl. As the L-homoserine derivative represented by Chemical Formula 1 and the first intermediate compound represented by Chemical Formula 3 have such functional groups, L-glufosinate with improved optical purity can be more easily prepared.

The first acid catalyst may be, for example, at least one selected from the group consisting of $CH_3COOH$, $HCl$, $H_2SO_4$, $HBr$ and $HI$.

The content of the first acid catalyst can be appropriately selected depending on the type of acid used. For example, the first acid catalyst may be used in an amount of 0.1 to 100 equivalents based on 1 equivalent of the first intermediate compound represented by Chemical Formula 2. Specifically, in the case of hydrochloric acid or sulfuric acid, it may be 0.1 to 2 equivalents, 0.3 to 1.8 equivalents, or 0.5 to 1.5 equivalents, and in the case of acetic acid, it may be 10 equivalents or more, 20 equivalents or more, 10 equivalents to 50 equivalents, or 20 to 40 equivalents. When the content of the first acid catalyst is too low, it may have a slight effect on the reaction rate, and when the content of the first acid catalyst is too large, by-products may increase.

The step of preparing the second intermediate compound may be carried out in the presence of a solvent, or may be carried out under neat conditions without a solvent. The solvent may be water or an organic solvent.

The organic solvent may be, for example, alcohol, toluene, benzene, tetrahydrofuran, acetone, chloroform, dichloromethane, acetonitrile, and the like. The alcohol may be, for example, methanol, ethanol, propanol, butanol, pentanol, or the like, without being limited thereto.

The step of preparing the second intermediate compound may be carried out at a temperature of, for example, 20 to 150° C., 20 to 100° C., 30 to 90° C., 40 to 80° C., or 50 to 70° C. The reaction time may be particularly at least 40° C., for example between 40 and 80° C. The step of preparing the second intermediate compound may be carried out, for example, for 0.1 to 20 hours, 0.1 to 15 hours, 0.1 to 10 hours, 0.1 to 6 hours, 0.5 to 5 hours, 1 to 4 hours, or 2 to 4 hours. As the lactone formation reaction is carried out within the above temperature range and time range, the second intermediate compound may be more easily prepared.

In the step of preparing the second intermediate compound, the yield of the second intermediate compound may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the step of preparing the second intermediate compound, the enantiomeric excess of the second intermediate compound having L-form may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more.

Then, the second intermediate compound represented by Chemical Formula 4 can be reacted with a halogenation agent and at least one $R_2$—OH to prepare the third intermediate compound represented by the following Chemical Formula 2.

The first intermediate compound represented by Chemical Formula 4 can be subjected to a halogenation/ring-opening reaction with a halogenation agent and at least one $R_2$—OH to prepare a third intermediate compound represented by the following Chemical Formula 2. For example, the halogenation/ring-opening reaction is proceeded by reacting the second intermediate compound represented by the following Chemical Formula 4 with a halogen of the halogenating agent, and then a substitution reaction with a $R_2$-functional group of the $R_2$—OH compound can proceed to thereby form a third intermediate compound.

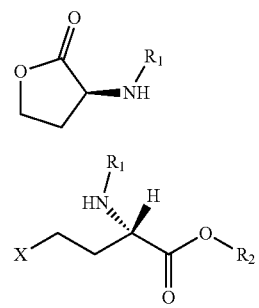

<Chemical Formula 4>

<Chemical Formula 2>

The halogenating agent may be, for example, at least one selected from HCl, HBr, HI, phosgene, $SOCl_2$, oxalyl chloride, a combination of triethylsilane with palladium chloride and methyl iodide (($C_2H_5)_3SiH$)+$PdCl_2$+$CH_3I$), $POCl_3$, $PCl_3$, $PCl_5$, $PBr_3$, $PI_3$, a combination of $H_2SO_4$ and KBr ($H_2SO_4$+KBr), a combination of P and $Cl_2$ (P+$Cl_2$), a combination of P and $Br_2$ (P+$Br_2$), a combination of P and $I_2$ (P+$I_2$), $TiCl_4$, $ZnCl_2$, and $BBr_3$. The halogenating agent may be particularly triethylsilane, $(CH_2CH_3)_3SiH$)+palladium chloride ($PdCl_2$)+methyl iodide ($CH_3I$), $SOCl_2$ and the like.

The content of the halogenating agent may be, for example, 1 to 10 equivalents, 1 to 5 equivalents, 1 to 4 equivalents, 1 to 3 equivalents, 1 to 2 equivalents, 1 to 1.5 equivalents, 0.1 to 1.3 equivalents, or 1 to 1.1 equivalents based on 1 equivalent of the second intermediate compound represented by Chemical Formula 4.

At least one $R_2$—OH compound may be used in the reaction to form a third intermediate compound. When plural $R_2$—OH compounds are used, the respective $R_2$—OH compounds may be the same as or different from each other.

The $R_2$—OH compound may be, for example, at least one selected from the group consisting of methanol, ethanol, n-propanol, iso-propanol, butanol, pentanol, hexanol, benzyl alcohol, phenol and naphthol. By selecting the aforementioned materials as the $R_2$—OH compound, a third intermediate compound can be obtained in a higher yield from the first intermediate compound.

The content of the $R_2$—OH compound may be, for example, 1 to 60 equivalents, 1 to 40 equivalents, 2 to 20 equivalents, or 3 to 10 equivalents based on 1 equivalent of the second intermediate compound.

In the step of preparing the third intermediate compound from the second intermediate, the halogenation reaction/ring-opening reaction may be carried out at a temperature of, for example, 20 to 100° C., 25 to 90° C., or 40 to 80° C.

In the step of preparing the third intermediate compound, the halogenation reaction/ring-opening reaction may be carried out, for example, for 0.1 to 30 hours, 1 to 30 hours, 5 to 30 hours, 10 to 30 hours, 15 to 25 hours, 17 to 23 hours, or 18 to 20 hours. As the halogenation reaction and the substitution reaction are carried out within the above temperature range and time range, a third intermediate compound, that is, a halogenated compound, can be more easily prepared.

In the step of preparing the third intermediate compound, the yield of the third intermediate compound may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the step of preparing the third intermediate compound, the enantiomeric excess of the third intermediate compound having L-form may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more.

According to one embodiment, the step (step a) of preparing the compound of Chemical Formula 2 from the compound of Chemical Formula 1 may include a step (step c-1) of preparing the compound of Chemical Formula 2 by reacting the compound of Chemical Formula 3 with a halogenating agent and at least one $R_2$—OH after the step b. That is, the first intermediate compound represented by the following Chemical Formula 3 can be reacted with a halogenation agent and at least one $R_2$—OH to prepare a third intermediate compound represented by the following Chemical Formula 2. For example, after a halogenation reaction is proceeded by reacting the first intermediate represented by Chemical Formula 3 with the halogen of the halogenating agent, a substitution reaction with the $R_2$-functional group of at least one $R_2$—OH can proceed to form a third intermediate compound.

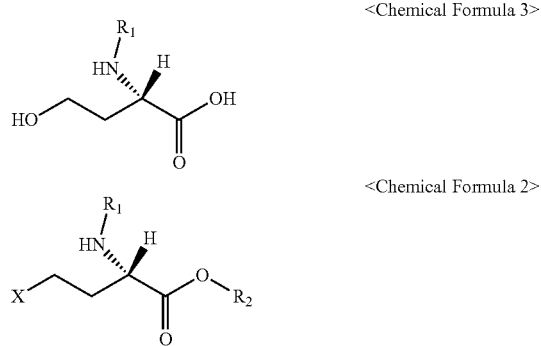

<Chemical Formula 3>

<Chemical Formula 2>

In the first intermediate compound represented by Chemical Formula 3 and the third intermediate compound represented by Chemical Formula 2, for example, $R_1$ may be $R_a$—(C=O)—, and $R_a$ may be hydrogen, a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms. Specifically, $R_1$ may be acetyl or succinyl.

Further, $R_2$ may be a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_d$), where $R_b$, $R_c$ and $R_d$ independently of one another are a substituted or unsubstituted alkyl group having 1 to 6 carbon atoms or a substituted or unsubstituted aryl group having 6 to 20 carbon atoms. Specifically, $R_2$ may be methyl, ethyl, propyl, butyl, pentyl, hexyl, benzyl, phenyl, naphthyl, —Si(CH$_3$)(tert-butyl)$_2$, —Si(C$_6$H$_5$)$_2$(tert-butyl), —Si(iso-propyl)$_3$, —Si(C$_5$H$_6$)(CH$_3$)$_2$, —Si(C$_6$H$_5$)$_2$(CH$_3$), —Si(C$_5$H$_6$)$_3$, —Si(CH$_3$)$_3$, —Si(CH$_2$CH$_3$)$_3$, —Si(CH$_2$CH$_3$)$_2$(CH$_3$), —Si(CH$_2$CH$_3$)(CH$_3$)$_2$, or —Si(tert-butyl)$_3$. As the first intermediate compound represented by Chemical Formula 3 and the third intermediate compound represented by Chemical Formula 2 have such functional groups, L-glufosinate having improved optical purity may be more easily prepared.

The halogenating agent may be, for example, at least one selected from HCl, HBr, HI, SOCl$_2$, oxalyl chloride, a combination of triethylsilane with palladium chloride and methyl iodide (($C_2H_5$)$_3$SiH)+PdCl$_2$+CH$_3$I), POCl$_3$, PCl$_3$, PCl$_5$, PBr$_3$, PI$_3$, a combination of H$_2$SO$_4$ and KBr (H$_2$SO$_4$+KBr), a combination of P and Cl$_2$ (P+Cl$_2$), a combination of P and Br$_2$ (P+Br$_2$), a combination of P and I$_2$ (P+I$_2$), TiCl$_4$, ZnCl$_2$, and BBr$_3$. The halogenating agent may be particularly HCl, triethylsilane, (CH$_2$CH$_3$)$_3$SiH)+palladium chloride (PdCl$_2$)+methyl iodide (CH$_3$I), SOCl$_2$, and the like.

The content of the halogenating agent may be, for example, 1 to 10 equivalents, 1 to 5 equivalents, 1 to 4 equivalents, 1 to 3 equivalents, 1 to 2 equivalents, 1 to 1.5 equivalents, 0.1 to 1.3 equivalents, or 1 to 1.1 equivalents based on 1 equivalent of the first intermediate compound represented by Chemical Formula 3.

At least one $R_2$—OH compound may be used in the reaction to form the third intermediate compound. When plural $R_2$—OH compounds are used, the respective $R_2$—OH compounds may be the same as or different from each other.

The $R_2$—OH compound may be, for example, at least one selected from the group consisting of methanol, ethanol, n-propanol, iso-propanol, butanol, pentanol, hexanol, benzyl alcohol, phenol and naphthol. By selecting the above materials as the $R_2$—OH compound, a third intermediate compound can be obtained in a higher yield from the first intermediate compound. The content of the $R_2$—OH compound may be, for example, 1 to 40 equivalents, 2 to 20 equivalents, or 3 to 10 equivalents based on 1 equivalent of the first intermediate compound.

The step of preparing the third intermediate compound may be carried out in the presence of a solvent or may be carried out under neat conditions without a solvent. The solvent may be an organic solvent.

The organic solvent may be, for example, alcohol, toluene, benzene, tetrahydrofuran, acetone, chloroform, dichloromethane, acetonitrile, and the like. Alcohol is, for example, methanol, ethanol, propanol, butanol, pentanol, and the like, without being limited thereto.

In the step of preparing the third intermediate compound, the halogenation reaction may be carried out at a temperature of, for example, 20 to 120° C., 20 to 80° C., 30 to 70° C., or 40 to 60° C. The step of preparing the third intermediate compound may be carried out, for example, for 0.1 to 30 hours, 1 to 30 hours, 5 to 30 hours, 10 to 30 hours, 15 to 25 hours, 17 to 23 hours, or 18 to 20 hours. As the halogenation reaction is carried out within the above temperature range and time range, the third intermediate compound, that is, the halogenated compound can be more easily prepared.

In the step of preparing the third intermediate compound, the yield of the third intermediate compound may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the step of preparing the third intermediate compound, the enantiomeric excess of the third intermediate compound with L-form may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more.

That is, by using the compound of Chemical Formula 1, which is an L-homoserine derivative, as a starting material, it is possible to prepare the L-glufosinate intermediate of Chemical Formula 2 without including the step of preparing the compound of Chemical Formula 4 from the compound of Chemical Formula 3. Accordingly, the preparation process of the L-glufosinate intermediate having high optical purity can be simplified.

According to another embodiment, the step (step a) of preparing the compound of Chemical Formula 2 from the compound of Chemical Formula 1 may include a step (step b-1) of preparing a compound of Chemical Formula 4 by reacting a compound of Chemical Formula 1 and a second acid catalyst.

More specifically, an L-homoserine derivative represented by the following Chemical Formula 1 can be reacted with a second acid catalyst to prepare a second intermediate compound represented by the following Chemical Formula 4. That is, the L-homoserine derivative represented by the following Chemical Formula 1 may be lactonized using a second acid catalyst to obtain a lactone compound represented by the following Formula 4.

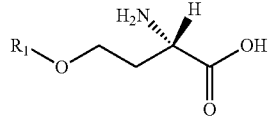
<Chemical Formula 1>

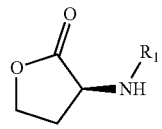
<Chemical Formula 4>

The second acid catalyst may be, for example, at least one selected from acetic acid, formic acid, butyric acid, pentanoic acid, and propionic acid. The second acid catalyst may be particularly acetic acid.

The content of the second acid catalyst may be 0.1 to 20 equivalents or 0.4 to 19 equivalents based on 1 equivalent of the L-homoserine derivative represented by Chemical Formula 1.

In the step of preparing the second intermediate compound, the lactone formation reaction may be carried out at a temperature of, for example, 20 to 100° C., 40 to 980° C., 60 to 95° C., or 70 to 90° C. The reaction temperature may be particularly at least 70° C., for example 70 to 90° C. In the step of preparing the second intermediate compound, the lactone formation reaction may be carried out, for example, for 1 to 20 hours, 2 to 18 hours, 4 to 17 hours, or 6 to 16 hours. As the lactone formation reaction is carried out within the above temperature range and time range, the second intermediate compound can be more easily prepared.

Then, a halogenation agent and at least one $R_2$—OH can be reacted from the prepared second intermediate to prepare a third intermediate compound. The details concerning the halogenating agent and $R_2$—OH are as described above.

That is, by using the compound of Formula 1, which is an L-homoserine derivative, as a starting material, the compound of Chemical Formula 4 is prepared without including the step of preparing the compound of Chemical Formula 3, and then, the L-glufosinate intermediate of Chemical Formula 2 can be prepared. Thereby, the preparation process of the L-glufosinate intermediate having high optical purity can be simplified. In addition, without the need to introduce a separate protecting group, the terminal group in the L-homoserine derivative can transfer to an amine group to prepare an intermediate compound containing an amine protecting group, so that charging of an additional compound may not be required for the introduction of a separate protecting group.

The preparation method of L-glufosinate of the present invention may be a method for preparing L-glufosinate from an L-homoserine derivative, the method comprising a step of preparing a compound of the following Chemical Formula 2 from the compound of the following Chemical Formula 1.

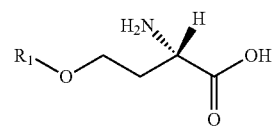
<Chemical Formula 1>

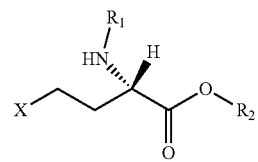
<Chemical Formula 2>

In the step of preparing the compound of Chemical Formula 2 from the compound of Chemical Formula 1, the above-mentioned matters concerning the method for preparing the L-glufosinate intermediate may be applied as they are.

If necessary, the method of preparing L-glufosinate may further include a step of preparing L-glufosinate from the third intermediate compound represented by Chemical Formula 2. In the following, a method of preparing L-glufosinate from the third intermediate compound of Chemical Formula 2 will be described.

By using the above-mentioned intermediate compound, it is possible to easily prepare L-glufosinate in a high yield. A fourth intermediate compound represented by the following Chemical Formula 6 can be prepared by reacting the third intermediate compound represented by Chemical Formula 2 with a phosphorus-based compound represented by the following Chemical Formula 5, or by reacting the second intermediate compound with the phosphorus-based compound represented by Chemical Formula 5.

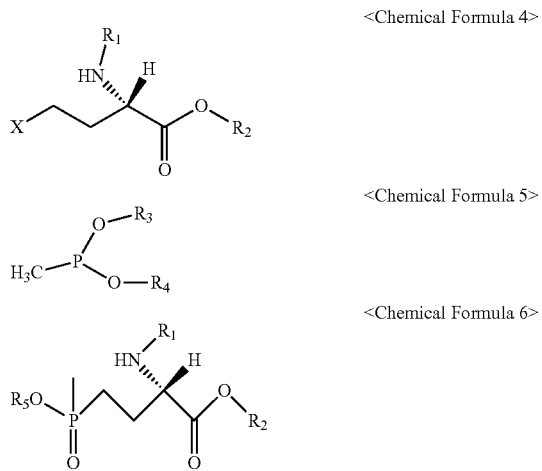

<Chemical Formula 4>

<Chemical Formula 5>

<Chemical Formula 6> where in the above formulas, $R_1$ is $R_a$—(C=O)—, where
$R_a$ is hydrogen, a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_d$), where $R_b$, $R_c$ and $R_d$ independently of one another are a substituted or unsubstituted alkyl group having 1 to 6 carbon atoms or a substituted or unsubstituted aryl group having 6 to 20 carbon atoms, $R_3$ and $R_4$ independently of one another are hydrogen, a substituted or unsubstituted alkyl group having 1 to 6 carbon atoms, a substituted or unsubstituted alkenyl group having 1 to 6 carbon atoms, or a substituted or unsubstituted alkynyl group having 1 to 6 carbon atoms $R_5$ is $R_3$ or $R_4$, X is halogen, and substituents of the alkyl group, alkenyl group, alkynyl group, cycloalkyl group, aryl group, and heteroaryl group independently of one another are at least one selected from hydrogen, halogen, a carboxyl group (—COOH), an amino group (—NH$_2$), a nitro group (—NO$_2$), a cyano group (—CN), an alkyl group having 1 to 6 carbon atoms, an aryl group having 6 to 10 carbon atoms, and a cycloalkyl group having 3 to 10 carbon atoms.

In the third intermediate compound represented by Chemical Formula 2, the phosphorus-based compound represented by Chemical Formula 5, and the fourth intermediate compound represented by Chemical Formula 6, for example, $R_1$ may be acetyl or succinyl, $R_2$ may be hydrogen, methyl, ethyl, propyl, butyl, pentyl, hexyl, benzyl, phenyl, naphthyl, —Si(CH$_3$)(tert-butyl)$_2$, —Si(C$_6$H$_5$)$_2$(tert-butyl), —Si(iso-propyl)$_3$, —Si(C$_5$H$_6$)(CH$_3$)$_2$, —Si(C$_6$H$_5$)$_2$(CH$_3$), —Si(C$_5$H$_6$)$_3$, —Si(CH$_3$)$_3$, —Si(CH$_2$CH$_3$)$_3$, —Si(CH$_2$CH$_3$)$_2$(CH$_3$), —Si(CH$_2$CH$_3$)(CH$_3$)$_2$, or —Si(tert-butyl)$_3$, and $R_3$ and $R_4$ may be any one selected from the group consisting of methyl, ethyl, propyl, butyl, pentyl and hexyl. As the third intermediate compound represented by Chemical Formula 2, the phosphorus-based compound represented by Chemical Formula 5, and the fourth intermediate compound represented by Chemical Formula 6 have such functional groups, L-glufosinate having improved optical purity can be more easily prepared. The phosphorus-based compound represented by Chemical Formula 5 may be particularly alkylmethylphosphonite, for example, diethylmethylphosphonite (DMP) or ethylmethylphosphinate (EMP), or butylmethylphosphinate (BMP).

The phosphorus-based compound represented by Chemical Formula 5 may be used in an amount of 0.5 to 10 equivalents, 0.7 to 8 equivalents, 0.9 to 7 equivalents, or 1 to 6 equivalents based on 1 equivalent of the third intermediate compound represented by Chemical Formula 2.

According to one embodiment, the third acid may be used in the process of preparing the fourth intermediate compound by reacting the third intermediate compound with the phosphorus-based compound or by reacting the second intermediate compound with the phosphorus-based compound represented by Chemical Formula 5.

The third acid is, for example, Lewis acid, and the Lewis acid may be, for example, at least one selected from KF+Al$_2$O$_3$, ZnCl$_2$ LiBr, ZnBr$_2$, BF$_3$-Et$_2$O (diehtylether), COCl$_2$, MgBr$_2$, BuP, Sc(OTf)$_3$ (OTf= trifluoromethanesulfonate), Sc(NTf$_2$)$_3$(scandium(III) trifluoromethanesulfonimide), TiCl$_3$-2AgClO$_4$, TiCl$_3$(OTf), Sn(OTf)$_2$, TMSOTf (TriMethylSilyl trifluoromethanesulfonate), La(OTf)$_3$, Cu(OTf)$_2$, and TaCl$_5$, and in particular, it may be KF+Al$_2$O$_3$.

The content of the third acid may be, for example, 0.1 to 100 parts by weight, 0.1 to 50 parts by weight, 0.1 to 40 parts by weight, 0.1 to 30 parts by weight, 0.1 to 20 parts by weight, 0.1 to 10 parts by weight, 0.1 to 5 parts by weight, or 0.1 to 2 parts by weight based on 100 parts by weight of the third intermediate compound represented by Chemical Formula 2. When the content of the third acid is too low, it may have a slight effect on the reaction rate, and when the content of the third acid is too high, by-products may increase. By using the third acid, the fourth intermediate compound can be obtained in a further improved yield.

According to one embodiment, the third acid may not be added in the above reaction. When the third acid is not added, the reaction time may increase and the reaction temperature may increase. For example, when the third acid is not used, the reaction may be carried out at a temperature of 120 to 180° C. for 1 to 20 hours.

The reaction temperature may be, for example, 80 to 180° C., 80 to 160° C., 90 to 160° C., 90 to 150° C., 100 to 160° C., 100 to 150° C., 100 to 140° C., 110 to 160° C., 110 to 150° C., 110 to 160° C., 110 to 140° C., 120 to 160° C., 120 to 150° C., or 120 to 140° C. Meanwhile, when an acid is added, the reaction temperature may be, for example, 80 to 160° C., and when no acid is added, the reaction time may increase and the reaction temperature may increase. For example, when an acid is not used, the reaction temperature may be 120 to 180° C.

In the step of preparing the fourth intermediate compound, the reaction may be carried out, for example, for 0.1 to 20 hours, 1 to 20 hours, 1 to 18 hours, 5 to 15 hours, 6 to 14 hours, 8 to 14 hours, 10 to 14 hours, or 11 to 13 hours.

The step of preparing the fourth intermediate compound may be carried out in the presence of a solvent, or may be carried out under neat conditions without a solvent. The solvent may be water or an organic solvent.

The organic solvent may be, for example, alcohol, toluene, benzene, tetrahydrofuran, acetone, chloroform, dichloromethane, acetonitrile, and the like. The alcohol may be, for example, methanol, ethanol, propanol, butanol, pentanol, or the like, without being limited thereto. When the tertiary acid is used and the solvent is water, the pH of the aqueous solution containing water may be 1 to 3. That is, in the step of preparing the fourth intermediate compound, the reaction solution may be an acidic aqueous solution with a pH of 1 to 3. As the reaction solution has a pH in this range, the fourth intermediate compound can be more easily prepared.

In the step of preparing the fourth intermediate compound, the reaction may be carried out at a temperature of, for example, 80 to 160° C., 90 to 160° C., 90 to 150° C., 100 to 160° C., 100 to 150° C., 100 to 140° C., 110 to 160° C., 110 to 150° C., 110 to 160° C., 110 to 140° C., 120 to 160° C., 120 to 150° C., or 120 to 140° C. In the step of preparing the fourth intermediate compound, the reaction may be carried out, for example, for 0.1 to 20 hours, 1 to 18 hours, 5 to 15 hours, 6 to 14 hours, 8 to 14 hours, 10 to 14 hours, or 11 to 13 hours. As the reaction is carried out within the above temperature range and time range, the fourth intermediate compound can be more easily prepared.

In the step of preparing the fourth intermediate compound, the yield of the fourth intermediate compound may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the step of preparing the fourth intermediate compound, the enantiomeric excess of the fourth intermediate compound having L-form may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more.

Finally, the fourth intermediate compound can be hydrolyzed under a fourth acid catalyst to prepare L-glufosinate represented by the following Chemical Formula 7. That is, the fourth intermediate compound represented by Formula 6 can be hydrolyzed under a fourth acid catalyst to remove terminal functional groups, thereby obtaining L-glufosinate represented by the following Chemical Formula 7.

<Chemical Formula 6>

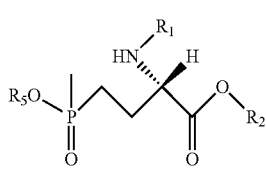

<Chemical Formula 7>

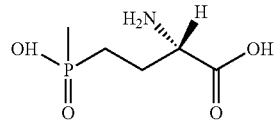

In the fourth intermediate compound represented by Chemical Formula 6, for example, $R_1$ may be acetyl or succinyl, $R_2$ may be each independently hydrogen, methyl, ethyl, propyl, butyl, pentyl, hexyl, benzyl, phenyl, naphthyl, —Si(CH$_3$)(tert-butyl)$_2$, —Si(C$_6$H$_5$)$_2$(tert-butyl), —Si(isopropyl)$_3$, —Si(C$_5$H$_6$)(CH$_3$)$_2$, —Si(C$_6$H$_5$)$_2$(CH$_3$), —Si(C$_5$H$_6$)$_3$, —Si(CH$_3$)$_3$, —Si(CH$_2$CH$_3$)$_3$, —Si(CH$_2$CH$_3$)$_2$(CH$_3$), —Si(CH$_2$CH$_3$)(CH$_3$)$_2$, or —Si(tert-butyl)$_3$, and $R_5$ may be $R_3$ or $R_4$. As the fourth intermediate compound represented by Chemical Formula 6 has such functional groups, L-glufosinate having improved optical purity can be more easily prepared.

The fourth acid is, for example, at least one selected from the group consisting of HCl, H$_2$SO$_4$, and a combination of KF and Al$_2$O$_3$(KF+Al$_2$O$_3$), but the fourth acid is not necessarily limited thereto, and the fourth acid can be used without limitation as long as it is used as an acid catalyst in the technical field. The fourth acid may be particularly hydrochloric acid.

The content of the fourth acid may be, for example, 0.1 to 100 parts by weight, 0.1 to 50 parts by weight, 0.1 to 40 parts by weight, 0.1 to 30 parts by weight, 0.1 to 20 parts by weight, 0.1 to 10 parts by weight, 0.1 to 5 parts by weight, or 0.1 to 2 parts by weight, based on 100 parts by weight of the fourth intermediate compound represented by Chemical Formula 6. When the content of the fourth acid is too low, it may have a slight effect on the reaction rate, and when the content of the fourth acid is too high, by-products may increase.

The step of preparing L-glufosinate may be carried out in the presence of a solvent, or may be performed in neat conditions without a solvent.

When the solvent is water during use of the fourth acid, the pH of the aqueous solution containing water may be 1 to 3. That is, in the step of preparing L-glufosinate, the reaction solution may be an acidic aqueous solution with a pH of 1 to 3. As the reaction solution has a pH in this range, L-glufosinate can be more easily prepared.

In the step of preparing L-glufosinate, the hydrolysis reaction may be carried out at a temperature of, for example, 20 to 150° C., 40 to 140° C., 60 to 130° C., 80 to 120° C., or 90 to 110° C. In the step of preparing L-glufosinate, the hydrolysis reaction may be carried out, for example, for 0.1 to 30 hours, 1 to 20 hours, 1 to 15 hours, 3 to 13 hours, 4 to 12 hours, 5 to 11 hours, 6 to 10 hours, 7 to 9 hours, 10 to 30 hours, 12 to 24 hours, 15 to 20 hours, or 15 to 18 hours. As the hydrolysis reaction is carried out within the above temperature range and time range, L-glufosinate can be more easily prepared.

In the step of preparing L-glufosinate, the yield of L-glufosinate may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

The enantiomeric excess of the prepared L-glufosinate may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more. As L-glufosinate has such an improved optical purity, for example, a further improved herbicide effect can be provided.

In the present invention, L-glufosinate may include its salt form. Specifically, the salt of L-glufosinate may be, for example, hydrochloride of L-glufosinate, sulfate of L-glufosinate, carbonate of L-glufosinate, ammonium salt of L-glufosinate, and the like, but are not necessarily limited thereto, and the salt can be used without limitation as long as it a salt of L-glufosinate obtained by the above-described glufosinate preparation method.

Example 1: Method for Preparing L-Glufosinate Intermediate Using O-Acetyl-L-Homoserine (Using Lactone Intermediate (1))

Step 1-1: Preparation of N-Acetyl-L-Homoserine

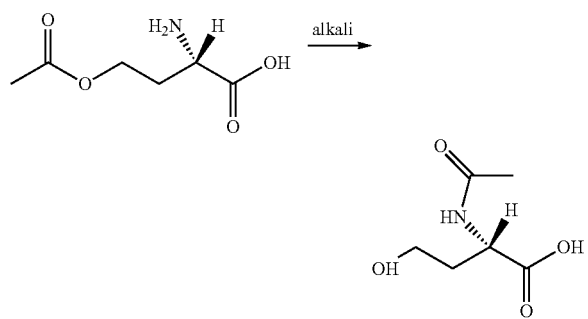

To an aqueous solution in which O-Acetyl-L-Homoserine (II) (1 g, 6.2 mmol) was dissolved in 30 mL of water, NaOH (40 wt. % aqueous solution) was slowly added to prepare a reaction solution with a pH of 9. Then, the prepared reaction solution was stirred at 25° C. for 30 minutes. Then, the reaction solution was heated to 50° C. and then stirred at 50° C. for 5 hours. Then, 1N HCl (aq) was added to the solution in which the reaction was completed, neutralized, and then concentrated under reduced pressure to prepare a concentrate. The prepared concentrate was cooled to 0° C., ethanol was added thereto, the mixture was stirred, and filtered under reduced pressure to obtain 0.98 g (yield: 98%) of N-Acetyl-L-Homoserine (III-1) as a white solid. The structure of N-Acetyl-L-Homoserine (III-1) was confirmed by NMR.

$^1$H NMR (400 MHz, DMSO-d6): δ 7.68 (d, J=8 Hz, 1H), 3.96 (m, 1H), 3.40 (t, J=6.8 Hz, 2H), 1.83 (s, 3H), 1.81 (m, 1H), 1.61 (m, 1H)

Step 1-2: Preparation of N-Acetyl-L-Homoserine lactone

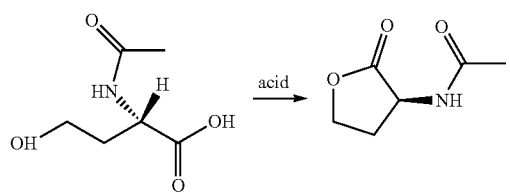

To an aqueous solution in which N-Acetyl-L-Homoserine (III-1) (1 g, 6.2 mmol) was dissolved in 30 mL of water, c-HCl (conc. hydrochloric acid) was slowly added to prepare a reaction solution with a pH of 2. The prepared reaction solution was stirred at 25° C. for 30 minutes. Then, the reaction solution was heated to 60° C. and then stirred at 60° C. for 3 hours. Then, 1N NaOH (aq) was added to the solution in which the reaction was completed, neutralized, and then concentrated under reduced pressure to prepare a concentrate. The prepared concentrate was cooled to 0° C., isopropanol was added thereto, the mixture was stirred, and filtered under reduced pressure to obtain 0.87 g (yield: 98%) of N-acetyl-L-homoserine lactone as a white solid. The structure of N-acetyl-L-homoserine lactone was confirmed by NMR.

$^1$H NMR (400 MHz, DMSO-d6): δ 3.96 (m, 1H), 3.89 (t, J=6.8 Hz, 2H), 1.91 (s, 3H), 2.11 (m, 1H), 1.83 (m, 1H)

Step 1-3: Preparation of Ethyl-2-(acetamino)-4-chlorobutanoate

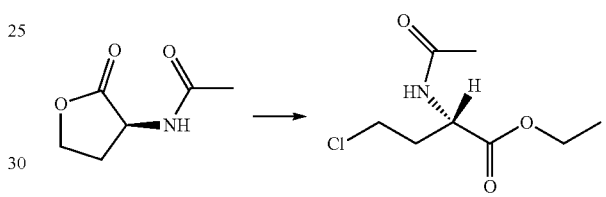

To a solution in which 4 g (28 mmol) of N-acetyl-L-homoserine lactone was dissolved in 60 mL of ethanol, thionyl chloride (6.6 g, 56 mmol) was slowly added at 0° C. to prepare a reaction solution. The prepared reaction solution was stirred at 80° C. for 3 hours. Then, 1N NaOH (aq) was added to the solution in which the reaction was completed, neutralized, and then concentrated under reduced pressure to prepare a concentrate. The prepared concentrate was diluted with ethyl acetate and washed once with brine. The organic layer was dried over anhydrous magnesium sulfate (MgSO$_4$), filtered, and the filtrate was concentrated under reduced pressure to obtain a residue containing ethyl-2 (acetylamino)-4-chlorobutanoate.

The resulting residue was separated by column chromatography (mobile phase, hexane:ethyl acetate=1:1) to obtain 5.12 g (yield: 88%) of ethyl-2-(acetylamino)-4-chlorobutanoate as a colorless oil. The structure of ethyl-2-(acetylamino)-4-chlorobutanoate was confirmed by NMR.

$^1$H NMR (400 MHz, DMSO-d6): δ 4.49 (m, 1H), 4.22 (q, 2H), 3.60 (t, 2H), 2.25 (m, 2H), 1.91 (s, 3H), 1.30 (t, 3H)

Step 1-4: Preparation of Ethyl-2-(acetamino)-4 (ethoxymethylphosphinyl)butanoate

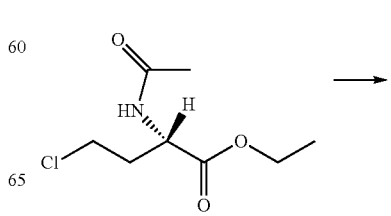

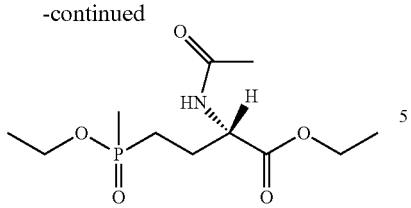

After ethyl-2-(acetamino)-4-chlorobutanoate (2.6 g, 12.6 mmol) and diethyl methylphosphonite (3.4 g, 25.2 mmol, 2 equiv.) were dissolved, nitrogen was injected therein, and then stirred at 120° C. for 12 hours. After completion of the reaction, unreacted diethylmethylphosphonite was removed at 80° C. under reduced pressure of 1 mmHg. The resulting residue was separated by column chromatography (mobile phase, ethyl acetate:isopropanol=4:1 volume ratio) to obtain 2.25 g (yield: 64%) of ethyl-2-(acetamino)-4-(ethoxymethylphosphinyl)butanoate as a colorless oil.

The structure of ethyl-2-(acetamino)-4-(ethoxymethylphosphinyl)butanoate was confirmed by NMR.

$^1$H NMR (400 MHz, CDCl3): δ 4.40 (m, 1H), 4.20 (q, 2H), 3.99 (q, 2H), 2.01 (m, 4H), 1.91 (s, 3H), 1.45 (d, J=14 Hz, 3H), 1.30 (t, 3H), 1.26 (t, 3H). 31P NMR (CDCl$_3$, 121.47 MHz) δ 54.28.

Step 1-5: Preparation of L-glufosinate (L-phosphinothricin)hydrochloride

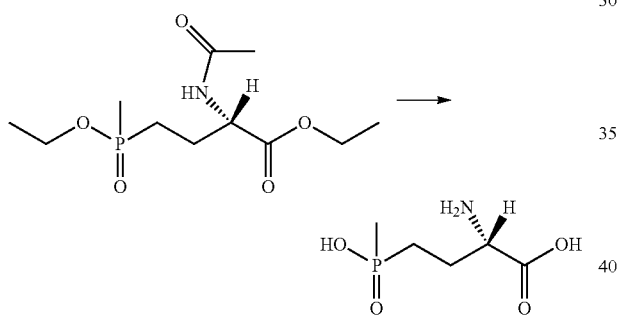

2 g (7.17 mmol) of ethyl-2-(acetamino)-4-(ethoxymethylphosphinyl)butanoate(V) was dissolved in 20 mL of 6N HCl, and then put into a sealing tube, and stirred at 120° C. for 15 hours. After completion of the hydrolysis reaction, the solvent was removed under reduced pressure to obtain 1.49 g of white L-glufosinate hydrochloride salt (yield: 96%; total yield of steps 1-1 to 1-5: 61%). The structure of L-glufosinate hydrochloride salt was confirmed by NMR.

$^1$H NMR (400 MHz, D2O): δ 4.12 (m, 1H), 2.45-1.65 (m, 4H), 1.46 (d, J=14 Hz, 3H).

Example 2: Preparation of L-Glufosinate Using O-Succinyl-L-Homoserine (Using Lactone Intermediate (2))

Step 2-1: Preparation of N-succinyl-L-homoserine

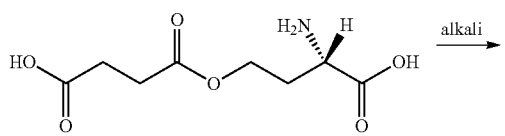

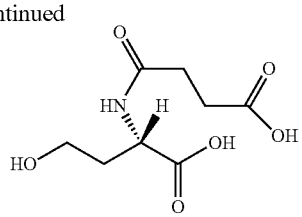

To an aqueous solution in which O-Succinyl-L-Homoserine(II) (1 g, 4.57 mmol) was dissolved in 30 mL of water, NaOH (40 wt. % aqueous solution) was slowly added to prepare a reaction solution with a pH 9.

Then, the prepared reaction solution was stirred at 25° C. for 30 minutes. Then, the reaction solution was heated to 50° C. and then stirred at 50° C. for 5 hours. Then, 1N HCl (aq) was added to the solution in which the reaction was completed, neutralized, and then concentrated under reduced pressure to prepare a concentrate. The prepared concentrate was cooled to 0° C., ethanol was added thereto, the mixture was stirred, and filtered under reduced pressure to obtain 0.98 g (yield: 98%) of N-succinyl-L-homoserine as a white solid. The structure of N-succinyl-L-Homoserine was confirmed by NMR.

$^1$H NMR (400 MHz, DMSO-d6): δ 7.68 (d, J=8 Hz, 1H), 3.96 (m, 1H), 3.40 (t, J=6.8 Hz, 2H), 2.55 (t, J=13 Hz, H), 2.31 (t, J=13 Hz, 2H), 1.83 (s, 3H), 1.81 (m, 1H), 1.61 (m, 1H)

White L-glufosinate hydrochloride salt (total yield of steps 2-2 to 2-5L: 51%) was obtained in the same manner as in Example 1, except for using N-succinyl-L-homoserine in the subsequent steps 2-2 to 2-5. The structure of L-glufosinate hydrochloride was confirmed by NMR.

$^1$H NMR (400 MHz, D2O): δ 4.12 (m, 1H), 2.45-1.65 (m, 4H), 1.46 (d, J=14 Hz, 3H).

Example 3: Preparation of L-Glufosinate Using O-Acetyl-L-Homoserine (without Using Lactone Intermediate (1))

Step 3-1: Preparation of N-acetyl-L-Homoserine

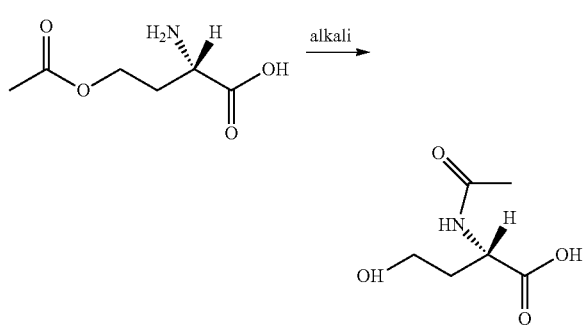

To an aqueous solution in which O-Acetyl-L-Homoserine (II) (1 g, 6.2 mmol) was dissolved in 30 mL of water, NaOH (40 wt. % aqueous solution) was slowly added as an alkali catalyst to prepare a reaction solution with a pH of 9. Then, the prepared reaction solution was stirred at 25° C. for 30 minutes. Then, the reaction solution was heated to 50° C. and stirred at 50° C. for 5 hours. Then, 1N HCl (aq) was added to the solution in which the reaction was completed, neutralized, and then concentrated under reduced pressure to prepare a concentrate. The prepared concentrate was cooled to 0° C., ethanol was added thereto, the mixture was stirred, and filtrated under reduced pressure to obtain 0.98 g (yield: 98%) of N-Acetyl-L-Homoserine (III-1) as a white solid. The structure of N-Acetyl-L-Homoserine was confirmed by NMR.

Step 3-2: Preparation of Ethyl-2-(acetamino)-4-chlorobutanoate

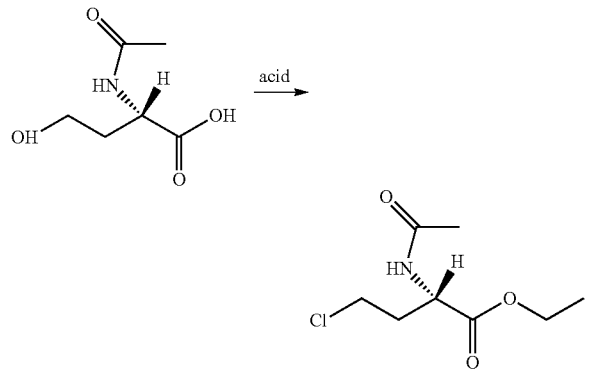

To a solution in which 3.85 g (24 mmol) of N-acetyl-L-Homoserine was dissolved in 60 mL of ethanol, 6.6 g (56 mmol) of thionyl chloride was slowly added at 0° C. to prepare a reaction solution. The prepared reaction solution was stirred at 80° C. for 3 hours.

Then, 1N NaOH (aq) was added to the solution where the reaction was completed, neutralized, and then concentrated under reduced pressure to prepare a concentrate. The prepared concentrate was diluted with ethyl acetate, and then washed once with brine. The organic layer was dried over anhydrous magnesium sulfate (MgSO$_4$), filtered, and the filtrate was concentrated under reduced pressure to obtain a residue containing ethyl-2-(acetylamino)-4-chlorobutanoate.

The resulting residue was separated by column chromatography (mobile phase, hexane:ethyl acetate=1:1) to obtain 5.12 g (yield: 88%) of ethyl-2-(acetylamino)-4-chlorobutanoate as a colorless oil. The structure of ethyl-2-(acetylamino)-4-chlorobutanoate was confirmed by NMR.

White L-Glufosinate hydrochloride salt (total yield of steps 3-3 to 3-4: 61%) was obtained in the same manner as in Example 1, except for using ethyl-2-(acetamino)-4-chlorobutanoate in the subsequent steps 3-3 to 3-4. The structure of L-glufosinate hydrochloride salt was confirmed by NMR.

Example 4: Preparation of L-Glufosinate Using O-Acetyl-L-Homoserine (without Using Lactone Intermediate (2))

Step 4-1: Preparation of N-acetyl-L-Homoserine

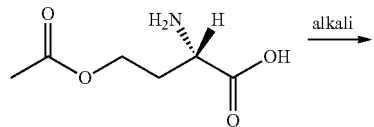

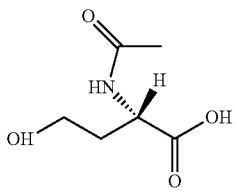

To an aqueous solution in which O-Acetyl-L-Homoserine (II) (1 g, 6.2 mmol) was dissolved in 30 mL of water, NaOH (40 wt. % aqueous solution) was slowly added to prepare a reaction solution with a pH of 9. Then, the prepared reaction solution was stirred at 25° C. for 30 minutes. Then, the reaction solution was heated to 50° C. and stirred at 50° C. for 5 hours. Then, 1N HCl (aq.) was added to the solution in which the reaction was completed, neutralized, and then concentrated under reduced pressure to prepare a concentrate. The prepared concentrate was cooled to 0° C., and then ethanol was added thereto, the mixture was stirred, stirred, and filtered under reduced pressure to obtain 0.98 g (yield: 98%) of N-Acetyl-L-Homoserine (III-1) as a white solid. The structure of N-Acetyl-L-Homoserine (III-1) was confirmed by NMR.

Step 4-2: Preparation of Triethylsilyl-2-(acetamino)-4-iodobutanoate

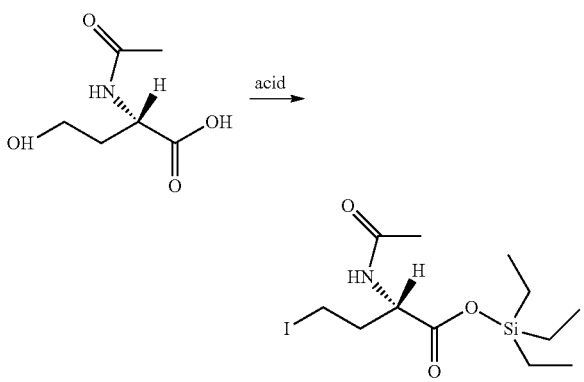

To a solution in which 3.85 g (24 mmol) of N-acetyl-L-homoserine was dissolved in 10 mL of ethanol, triethylsilane (4.9 mL, 31 mmol) was added slowly at 0° C. Then, methyl iodide (7.9 g, 56 mmol) and palladium chloride (100 mg, 0.56 mmol) were slowly added at the same temperature to prepare a reaction solution. The prepared reaction solution was stirred at 110° C. for 18 hours. Then, 1N NaOH (aq) was added to the solution in which the reaction was completed, neutralized, and then concentrated under reduced pressure to prepare a concentrate. The prepared concentrate was diluted with ethyl acetate and washed once with brine. The organic layer was dried over anhydrous magnesium sulfate (MgSO$_4$), filtered, and the filtrate was concentrated under reduced pressure. Thereby, a residue containing triethylsilyl-2-(acetylamino)-4-iodobutanoate was obtained. The obtained residue was separated by column chromatography (mobile phase, hexane: ethyl acetate=1:1) to obtain 4.16 g (yield: 44%) of triethylsilyl-2-(acetylamino) 4-chlorobutanoate as a colorless oil. The structure of triethylsilyl-2-(acetylamino)-4-chlorobutanoate was confirmed by NMR.

White L-glufosinate hydrochloride salt (total yield of steps 4-3 and 4-4: 61%) was obtained in the same manner as in Example 1, except for using triethylsilyl-2-(acetamino)-4-chlorobutanoate in the subsequent steps 4-3 and 4-4. The structure of L-glufosinate hydrochloride salt was confirmed by NMR.

Example 5: Preparation of L-Glufosinate Using O-Succinyl-L-Homoserine (without Using Lactone Intermediate (1))

Step 5-1: Preparation of N-Succinyl-L-Homoserine

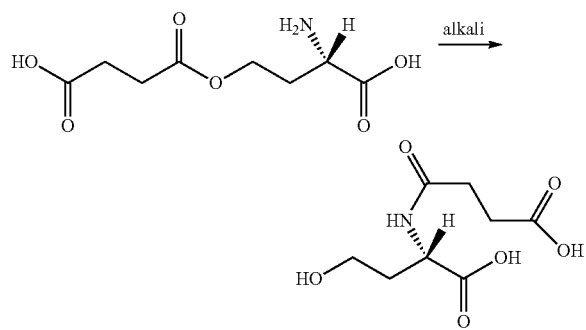

To an aqueous solution in which O-succinyl-L-homoserine(II) (1 g, 4.57 mmol) was dissolved in 30 mL of water, NaOH (40 wt. % aqueous solution) was slowly added to prepare a reaction solution with a pH of 9. Then, the prepared reaction solution was stirred at 25° C. for 30 minutes. Then, the reaction solution was heated to 50° C. and stirred at 50° C. for 5 hours. Then, 1N HCl (aq) was added to the solution in which the reaction was completed, neutralized, and then concentrated under reduced pressure to prepare a concentrate. The prepared concentrate was cooled to 0° C., ethanol was added thereto, the mixture was stirred, and filtrated under reduced pressure. Thereby, 0.98 g (yield: 98%) of N-succinyl-L-homoserine (III-1) as a white solid was obtained. The structure of N-succinyl-L-homoserine was confirmed by NMR.

White L-glufosinate hydrochloride salt (total yield of steps 5-2 to 5-4: 61%) was obtained in the same manner as in Example 3, except for using N-succinyl-L-homoserine in the subsequent steps 5-2 to 5-4. The structure of L-glufosinate hydrochloride salt was confirmed by NMR.

Example 6: Preparation of L-Glufosinate Using O-(Acetyl)-L-Homoserine

Step 6-1; Preparation of N-acetyl-L-Homoserine

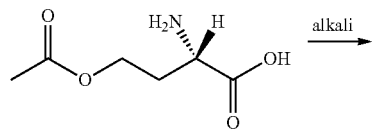

-continued

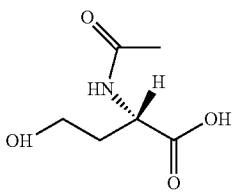

O-Acetyl-L-homoserine(II) (1 g, 6.2 mmol) was slowly added in an amount corresponding to 18.2 equivalents of acetic acid (6.77 g, 112.8 mmol) to prepare a reaction solution with a pH of 1. The prepared reaction solution was stirred at 90° C. for 6 hours. Then, the reaction solution was cooled to 60° C. and stirred for 3 hours. Then, 1N NaOH (aq) was added to the solution in which the reaction was completed, neutralized, and concentrated under reduced pressure to prepare a concentrate. The prepared concentrate was cooled to 0° C., isopropanol was added thereto, the mixture was stirred, and filtered under reduced pressure. Thereby, 0.8 g (yield: 90%) of N-acetyl-L-homoserine lactone as a white solid was obtained. The structure of N-acetyl-L-homoserine lactone was confirmed by NMR.

White L-glufosinate hydrochloride salt (total yield of steps 6-2 to 6-4: 61%) was obtained in the same manner as in Example 1, except for using N-acetyl-L-homoserine lactone in the subsequent steps 6-2 to 6-4. The structure of L-glufosinate hydrochloride salt was confirmed by NMR.

Comparative Example 1: Preparation of Racemic Glufosinate

Glufosinate was prepared according to the method disclosed in Example 1 of U.S. Pat. No. 6,359,162. The prepared glufosinate was a racemic mixture.

Comparative Example 2: Comparison with the Method for Producing L-Glufosinate which Introduces a Protecting Group into Homoserine Lactone L-glufosinate was prepared according to the following Reaction Scheme 1.

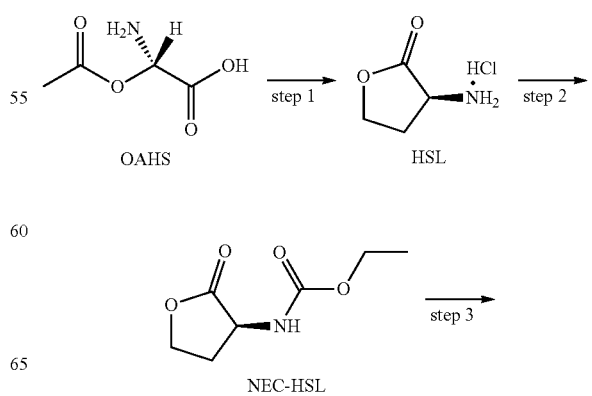

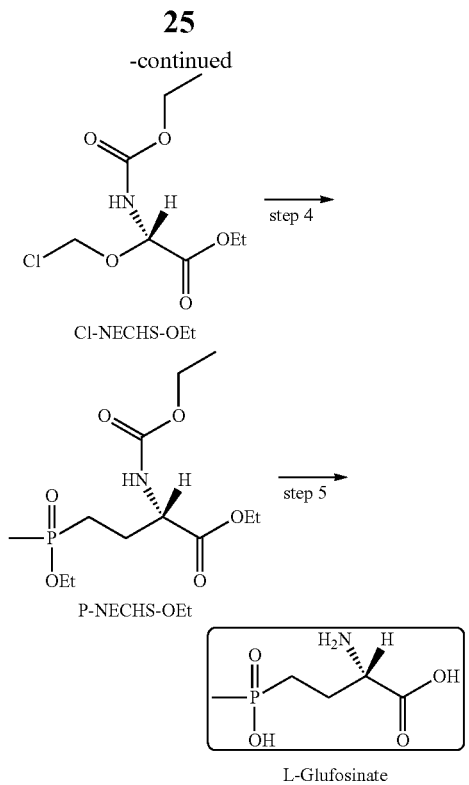

Cl-NECHS-OEt

P-NECHS-OEt

L-Glufosinate

The reaction conditions and reaction results of each reaction step are shown in Table 1 below.

TABLE 1

| Reaction section | Reaction route | Reaction condition | Reaction result |
|---|---|---|---|
| step 1 | OAH to HSL | HCl 6eq, 60° C. | HSL 95% |
|  |  | HCl 7eq, 60° C. | HSL 96% |
|  |  | HCl 8eq, 60° C. | HSL 97% |
| step 2 | HSL to NecHSL | Ethylchloroformate 1.2eq, pH 5 | NecHSL 95% |
|  |  | Ethylchloroformate 1.2eq, pH 3 | NecHSL 90% |
|  |  | Ethylchloroformate 1.2eq, pH 1.5 | NecHSL 54% |
| step 3 | NecHSL to Cl-NecHS-OEt | SOCl$_2$ 2eq, EtOH 40eq, 50° C. 16 h | Cl-NecHS-Oet 33% |
|  |  | SOCl$_2$ 2eq, EtOH 40eq, 50° C. 5 h | Cl-NecHS-Oet 26.9% |
|  |  | SOCl2 2eq, EtOH 10eq, RT, 3 h | Cl-NecHS-Oet 72.3% |
|  |  | SOCl2 2eq, EtOH 3.7eq, RT, 3 h | Cl-NecHS-Oet 85.4% |
|  |  | SOCl2 2eq, EtOH 3.7eq, 60° C. 3 h | Cl-NecHS-Oet 98.7% |
| step 4 & 5 | Cl-NecHS-OEt to L-GluF | DMP 2eq 150° C. 16 h/6N HCl 20 times, 120° C. 14 h | GluF 66.02% |
|  |  | DMP 2eq 140° C. 16 h/6N HCl 20 times, 120° C. 14 h | GluF 73.4% |
|  |  | DMP 2eq 120° C. 14 h/6N HCl 20 times, 120° C. 14 h | GluF 61.7% |

(OAHS: O-Acetylhomoserine, HSL: Homoserine lactone, NecHSL: N-ethoxycarbonyl-homoserine lactone, Cl-NecHSL-OEt: Ethyl-2-(ethoxycarbonylamino)-4-chlorobutanoate, P-NecHSL-OEt: Ethyl-2-(ethoxycarbonylamino)-4-(ethoxymethylphosphinyl)butanoate)

As shown in Table 1, when hydrochloric acid is used in the preparation of a lactone compound from an L-homoserine derivative, homoserine lactone shown in Reaction Scheme 1 is obtained instead of the second intermediate compound of Chemical Formula 3. The homoserine lactone is obtained, and an amine group in the homoserine lactone is protected with an ethoxycarbonyl group, which is then halogenated with a halogenating agent, bonded with a phosphorus-based compound, and hydrolyzed to prepare L-glufosinate. Thereby, it was confirmed that L-glufosinate is obtained in a low yield.

Experimental Example 1: Measurement of Enantiomeric Excess (% ee)

The enantiomeric excess of the L-glufosinate synthesized in Examples 1 to 6 and Comparative Example 1 is measured using chiral HPLC, and the results are shown in Table 1 below.

Chiral HPLC analysis was carried out with reference to the method disclosed in J. Chromatogr. 368, 413 (1986).

The enantiomeric excess (% ee) was determined using Sumichiral OA6100 (4.6×150 mm), Chiracel® OD-H (4.6×250 mm), Sumichiral OA5000 (4.6×150 mm), or Chiralpak zwix (4.0×150 mm) chiral column. As the mobile phase, a co-solvent of 0-30% methanol, 0-70% acetonitrile and 0-70% distilled water, or 2 mM copper sulfate aqueous solution was used, the solvent flow rate was 1.0 m/min, the sample injection amount was 10 μL, and the UV detection wavelength was 200 nm to 280 nm.

TABLE 2

|  | Enantiomeric excess [% ee] |
|---|---|
| Example 1 | 94 |
| Example 2 | 94 |
| Example 3 | 94 |
| Example 4 | 94 |
| Example 5 | 94 |
| Example 6 | 94 |
| Comparative Example 1 | less than 1 |

As shown in Table 2, in the case of the glufosinate prepared in Examples 1 to 6, the enantiomeric excess of L-glufosinate was significantly as compared with the glufosinate prepared in Comparative Example 1. Therefore, it is possible to simply prepare L-glufosinate with high yield and high purity by the preparation method including the intermediate compound of the present invention.

Experimental Example 2: Examination of pH Conditions when Preparing the First Intermediate Compound from an L-Homoserine Derivative The pattern obtained according to the pH of the first intermediate compound represented by Chemical Formula 2 from the L-homoserine derivative represented by Chemical Formula 1 was confirmed. N-acetyl-L-Homoserine, which is a first intermediate compound, was obtained in the same manner as in the preparation method of Example 1 (step 1-1) by using a starting material, O-Acetyl-L-homoserine as an L-homoserine derivative, provided that the pH during the reaction was changed to 8.2, 9.2, 10.2, 12.7 and 13.4, respectively, and the results are shown in Table 3 below.

TABLE 3

| Reaction condition | Reaction result |
|---|---|
| 8.2 | NAHS 12.2%/OAHS 87.8% |
| 9.2 | NAHS 50.8%/OAHS 49.2% |
| 10.2 | NAHS 93.9%/OAHS 6.1% |
| 12.7 | NAHS 100%/OAHS 0% |
| 13.4 | NAHS 100%/OAHS 0% |

(O-Acetyl-L-Homoserine, NAHS: N-Acetyl-L-Homoserine)

As shown in Table 3, when preparing the first intermediate compound represented by Chemical Formula 2 from the L-homoserine derivative represented by Chemical Formula 1, the yield of N-acetyl-L-Homoserine increased as the pH increased, especially, when the pH was 9 or higher, N-acetyl-L-Homoserine was obtained in high yield.

Experimental Example 3: Examination of the Reaction Conditions when Preparing the Second Intermediate Compound from the First Intermediate Compound The pattern obtained according to the reaction conditions of the second intermediate compound represented by Chemical Formula 4 from the first intermediate compound represented by Chemical Formula 3 was confirmed. N-acetyl-L-homoserine lactone, which is a second intermediate compound, was obtained in the same manner as in the preparation method of Example 1 (step 1-2) by using N-acetyl-L-homoserine as the first intermediate compound, provided that the equivalent of the acid during the reaction and the reaction temperature were changed as shown in Tables 3 to 5, respectively, and the results are shown in Tables 4 to 6 below.

TABLE 4

| Acid | Main variable | Reaction condition | Reaction result |
|---|---|---|---|
| Acetic acid | Acetic acid equivalent | 1.3 equiv. | NAHSL 37.4%/NAHS 58.3% |
| | | 2.6 equiv. | NAHSL 72.1%/NAHS 24.5% |
| | | 7.8 equiv. | NAHSL 93.1%/NAHS 3.0% |
| | | 13 equiv. | NAHSL 95.0%/NAHS 1.1% |
| | | 18.2 equiv. | NAHSL 96.0%/NAHS 1.1% |
| | Reaction temperature | 25° C. | NAHSL 23.1%/NAHS 71.3% |
| | | 40° C. | NAHSL 63.1%/NAHS 30.3% |
| | | 60° C. | NAHSL 93.1%/NAHS 3.0% |
| | | 70° C. | NAHSL 93.7%/NAHS 2.7% |
| | | 100° C. | NAHSL 92.2%/NAHS 1.2% |

(NAHS: A-Acetyl-L-Homoserine, NAHSL: A-acetyl-L-Homoserine lactone)

As shown in Table 4, when preparing a second intermediate compound represented by Chemical Formula 4 from the first intermediate compound represented by Chemical Formula 3 using acetic acid, the yield of N-acetyl-L-homoserine lactone increased as the acetic acid equivalent increased, and in particular, when the acetic acid equivalent was 2.6 or more, N-acetyl-L-homoserine lactone was obtained in high yield.

As the reaction temperature increased, the yield of N-acetyl-L-homoserine lactone increased, and in particular, when the reaction temperature was 40° C. or higher, N-acetyl-L-homoserine lactone was obtained in high yield.

TABLE 5

| Acid | Main variable | Reaction condition | Reaction result |
|---|---|---|---|
| Hydrochloric acid | Hydrochloric acid equivalent | 0.5 equiv. | NAHSL 16.4%/NAHS 80.7% |
| | | 0.75 equiv. | NAHSL 16.7%/NAHS 81.7% |
| | | 1.0 equiv. | NAHSL 72.7%/NAHS 22.4% |
| | | 1.25 equiv. | NAHSL 65.5%/NAHS 17.5% |
| | | 1.5 equiv. | NAHSL 43.8%/NAHS 9.9% |

As shown in Table 5, when preparing a second intermediate compound represented by Chemical Formula 4 from the first intermediate compound represented by Chemical Formula 3 using hydrochloric acid, the yield of N-acetyl-L-Homoserine lactone increased as the hydrochloric acid equivalent increased up to 1.0, and when applying 1.25 equivalents or more of hydrochloric acid, the yield of N-acetyl-L-homoserine lactone gradually decreased.

TABLE 6

| Acid | Main variable | Reaction condition | Reaction result |
|---|---|---|---|
| Sulfuric acid | Sulfuric acid equivalent | 0.5 equiv. | NAHSL 54.2%/NAHS 44.4% |
| | | 1.0 equiv. | NAHSL 61.4%/NAHS 14.9% |
| | | 1.5 equiv. | NAHSL 38.9%/NAHS 8.2% |
| | | 2.0 equiv. | NAHSL 23.0%/NAHS 4.4% |

As shown in Table 6, when preparing a second intermediate compound represented by Chemical Formula 4 from the first intermediate compound represented by Chemical Formula 3 using sulfuric acid, the yield of N-acetyl-L-homoserine lactone increased as the sulfuric acid equivalent increased up to 1.0, and when applying 1.5 equivalents or more of sulfuric acid, the yield of N-acetyl-L-homoserine lactone gradually decreased.

Experimental Example 4: Examination of Reaction Conditions when Preparing a Second Intermediate Compound from an L-Homoserine Derivative (without Using the First Intermediate Compound)

The pattern obtained according to the reaction conditions of the second intermediate compound represented by Chemical Formula 4 from the L-homoserine derivative represented by Chemical Formula 1 was confirmed.

A reaction solution in which O-acetyl-L-homoserine (II) (1 g, 6.2 mmol) was dissolved by slowly adding an acid without a separate solvent was prepared, and stirred for 30 minutes. Then, the reaction solution was heated up to the reaction temperature shown in Tables 6 to 10 below, and then stirred for the corresponding reaction time. Then, the solution in which the reaction was completed was concentrated under reduced pressure to prepare a concentrate, which was then cooled to 0° C., isopropanol was added thereto, the mixture was stirred, and filtered under reduced pressure. The yield of N-acetyl-L-homoserine lactone as a while solid was confirmed. The results according to each reaction condition are shown in Tables 7 to 11 below.

TABLE 7

| Acid | Main variable | Reaction condition | Reaction result |
|---|---|---|---|
| Acetic acid | Reaction temperature | 25° C., 6 hr | NAHSL 16.1% /OAHS 81.9% |
| | | 70° C., 6 hr | NAHSL 70.5%/OAHS 19.4% |
| | | 90° C., 6 hr | NAHSL 87.9%/OAHS 0% |
| | | 150° C., 6 hr | NAHSL 85.1%/OAHS 0% |
| | Reaction temperature | 90° C., 3 hr | NAHSL 69.3%/OAHS 20.0% |
| | | 90° C., 6 hr | NAHSL 83.5%/OAHS 5.1% |
| | | 90° C., 15 hr | NAHSL 87.9%/OAHS 0% |
| Acetic acid | Acetic acid equivalent | 1 equiv. | NAHSL 23.2%/OAHS 75.1% |
| | | 1.3 equiv. | NAHSL 32.5%/OAHS 59.2% |
| | | 13 equiv. | NAHSL 87.9%/OAHS 0% |
| | | 18 equiv. | NAHSL 90.2%/OAHS 0% |

As shown in Table 7, when preparing the second intermediate compound represented by Chemical Formula 4 from the L-homoserine derivative represented by Chemical Formula 1 using acetic acid, the yield of N-acetyl-L-Homoserine lactone increased as the acetic acid equivalent increased, and in particular, when the equivalent of acetic acid was 1.3 or more, N-acetyl-L-Homoserine lactone was obtained in high yield.

As the reaction temperature increased, the yield of N-acetyl-L-homoserine lactone increased, and in particular, when the reaction temperature was 70° C. or higher, N-acetyl-L-homoserine lactone was obtained in high yield.

As the reaction time increased, the yield of N-acetyl-L-homoserine lactone increased, and in particular, when the reaction time was 6 hours or more, N-acetyl-L-homoserine lactone was obtained in high yield.

TABLE 8

| Acid | Main variable | Reaction condition | Reaction result |
|---|---|---|---|
| Hydrochloric acid | Hydrochloric acid equivalent | 0.5 eq, 70° C. 2 h | HSL 12.3%/AH 81.4% |
| | | 0.75 eq, 70° C. 2 h | HSL 15.4%/AH 87.7% |
| | | 1.0 eq, 70° C. 2 h | HSL 25.9%/AH 71.4% |
| | | 1.25 eq, 70° C. 2 h | HSL 55.5%/AH 37.5% |
| | | 1.5 eq, 70° C. 2 h | HSL 73.8%/AH 20.9% |

TABLE 9

| Acid | Main variable | Reaction condition | Reaction result |
|---|---|---|---|
| Sulfuric acid | Sulfuric acid equivalent | 0.5 eq, 70° C. 2 h | HSL 50.1%/AH 41.4% |
| | | 1.0 eq, 70° C. 2 h | HSL 92.4%/AH 6.7% |
| | | 1.5 eq, 70° C. 2 h | HSL 98.9%/AH 0% |
| | | 2.0 eq, 70° C. 2 h | HSL 98.8%/AH 0% |

As shown in Tables 8 and 9, when applying hydrochloric acid or sulfuric acid as an acid, it was confirmed that N-acetyl-L-homoserine lactone, which is a second intermediate compound, is not obtained, L-homoserine lactone (AH) is produced, and thus, it is not suitable to use hydrochloric acid or sulfuric acid.

TABLE 10

| Acid | Main variable | Reaction condition | Reaction result |
|---|---|---|---|
| Formic acid | Formic acid equivalent | 1 eq, 90° C. | NAHSL 10.3%/OAHS 85.1% |
| | | 1.3 eq, 90° C. | NAHSL 18.5%/OAHS 75.2% |
| | | 13 eq, 90° C. | NAHSL 71.2%/OAHS 7.0% |
| | | 18.2 eq, 90° C. | NAHSL 80.2%/OAHS 0% |

As shown in Table 10, a second intermediate compound represented by Chemical Formula 4 can be obtained from the L-homoserine derivative represented by Chemical Formula 1 using formic acid, and the yield of N-acetyl-L-homoserine lactone increased as the formic acid equivalent increased.

TABLE 11

| Acid | Main variable | Reaction condition | Reaction result |
|---|---|---|---|
| Propionic acid | Propionic acid equivalent | 1 eq, 90° C. | NAHSL 21.2%/OAHS 75.1% |
| | | 1.3 eq, 90° C. | NAHSL 35.5%/OAHS 56.9% |
| | | 13 eq, 90° C. | NAHSL 80.8%/OAHS 0% |
| | | 18.2 eq, 90° C. | NAHSL 88.3%/OAHS 0% |

As shown in Table 11, when propionic acid was used, a second intermediate compound represented by Chemical Formula 4 could be obtained from the L-homoserine derivative represented by Chemical Formula 1 in a yield similar to that of acetic acid. As the propionic acid equivalent increased, the yield of N-acetyl-L-homoserine lactone increased.

Experimental Example 5: Examination of Reaction Conditions when Preparing a Third Intermediate Compound from the Second Intermediate Compound The pattern obtained according to the reaction conditions of the third intermediate compound represented by Chemical Formula 2 from the second intermediate compound represented by Chemical Formula 4 was confirmed. The third intermediate compound, ethyl-2-(acetamino)-4-chlorobutanoate or methyl-2-(acetamino)-4-chlorobutanoate was obtained in the same manner as in the preparation method of Example 1 (Steps 1-3) by using N-acetyl-L-homoserine lactone as a second intermediate compound, provided that the equivalent of ethanol or methanol and the reaction temperature during the reaction were changed as shown in Tables 12 and 13 below, respectively, and the results are also shown in Tables 12 and 13 below.

TABLE 12

| Alcohol | Main variable | Reaction condition | Reaction result |
|---|---|---|---|
| Ethanol | Ethanol equivalent | 1 eq, 80° C. $SOCl_2$ 2eq | Cl-NAHS-OEt 42.6% |
| | | 3 eq, 80° C. $SOCl_2$ 2eq | Cl-NAHS-OEt 93.0% |
| | | 3.7 eq, 80° C. $SOCl_2$ 2eq | Cl-NAHS-OEt 98.7% |
| | | 10 eq, 80° C. $SOCl_2$ 2eq | Cl-NAHS-OEt 63.0% |
| | | 20 eq, 80° C. $SOCl_2$ 2eq | Cl-NAHS-OEt 39.1% |
| | Reaction temperature | 3.7 eq, 0° C. $SOCl_2$ 2eq | Cl-NAHS-OEt 0% |
| | | 3.7 eq, 25° C. $SOCl_2$ 2eq | Cl-NAHS-OEt 12.6% |
| | | 3.7 eq, 40° C. $SOCl_2$ 2eq | Cl-NAHS-OEt 60.8% |
| | | 3.7 eq, 60° C. $SOCl_2$ 2eq | Cl-NAHS-OEt 97.5% |
| | | 3.7 eq, 80° C. $SOCl_2$ 2eq | Cl-NAHS-OEt 98.7% |

(NAHSL: N-acetyl-L-Homoserine lactone, Cl-NAHS-OEt: Ethyl-2-(acetamino)-4-chlorobutanoate)

As shown in Table 12, when a third intermediate compound represented by Chemical Formula 2 was prepared from the second intermediate compound represented by Chemical Formula 4 using ethanol, the yield of ethyl-2-(acetamino)-4-chlorobutanoate increased as the ethanol equivalent increased, and in particular, when the ethanol equivalent was 3 to 10 equivalents, ethyl-2-(acetamino)-4-chlorobutanoate was obtained in high yield. As the reaction temperature increased, the yield of ethyl-2-(acetamino)-4-chlorobutanoate increased, and in particular, when the reaction temperature was 40° C. or higher, ethyl-2-(acetamino)-4-chlorobutanoate was obtained in high yield.

TABLE 13

| Alcohol | Main variable | Reaction condition | Reaction result |
|---|---|---|---|
| Methanol | Methanol equivalent | 1 eq, 60° C. $SOCl_2$ 2eq | Cl-NAHS-OMe 63.2% |
| | | 3 eq, 60° C. $SOCl_2$ 2eq | Cl-NAHS-OMe 93.4% |
| | | 3.7 eq, 60° C. $SOCl_2$ 2eq | Cl-NAHS-OMe 99.6% |
| | | 20 eq, 60° C. $SOCl_2$ 2eq | Cl-NAHS-OMe 33.4% |
| | | 50 eq, 60° C. $SOCl_2$ 2eq | Cl-NAHS-OMe 26.6% |
| | Reaction temperature | 3.7 eq, 0° C. $SOCl_2$ 2eq | Cl-NAHS-OMe 0% |
| | | 3.7 eq, 25° C. $SOCl_2$ 2eq | Cl-NAHS-OMe 28.9% |
| | | 3.7 eq, 40° C. $SOCl_2$ 2eq | Cl-NAHS-OMe 85.6% |
| | | 3.7 eq, 60° C. $SOCl_2$ 2eq | Cl-NAHS-OMe 99.6% |

(NAHSL: N-acetyl-L-Homoserine lactone, Cl-NAHS-OMe: Methyl-2-(acetamino)-4-chlorobutanoate)

As shown in Table 13, when preparing a third intermediate compound represented by Chemical Formula 2 from the second intermediate compound represented by Chemical Formula 4 using methanol, the yield of methyl-2-(acetamino)-4-chlorobutanoate increased as the methanol equivalent increased, and in particular, when the methanol equivalent was 3 to 10 equivalents, methyl-2-(acetamino)-4-chlorobutanoate was obtained in high yield.

As the reaction temperature increased, the yield of methyl-2-(acetamino)-4-chlorobutanoate increased, and in particular, when the reaction temperature was 40° C. or higher, methyl-2-(acetamino)-4-chlorobutanoate was obtained in high yield.

Experimental Example 6: Examination of Reaction Conditions when Preparing a Third Intermediate Compound from the First Intermediate Compound The pattern obtained according to the reaction conditions of the third intermediate compound represented by Chemical Formula 2 from the first intermediate compound represented by Chemical Formula 3 was confirmed. A third intermediate compound was obtained in the same manner as in the preparation method of Example 3 (step 3-2), except for using N-acetyl-L-homoserine as the first intermediate compound, provided that the equivalent of alcohol and the reaction temperature during the reaction were changed as shown in Tables 14 to 17, respectively, and the results are also shown in Tables 14 to 17.

TABLE 14

| Alcohol | Main variable | Reaction condition | Reaction result |
|---|---|---|---|
| Methanol | Methanol equivalent | 1 eq, 60° C. $SOCl_2$ 2eq | Cl-NAHS-OMe 24.5% |
| | | 3 eq, 60° C. $SOCl_2$ 2eq | Cl-NAHS-OMe 78.4% |
| | | 3.7 eq, 60° C. $SOCl_2$ 2eq | Cl-NAHS-OMe 88.1% |
| | | 10 eq, 60° C. $SOCl_2$ 2eq | Cl-NAHS-OMe 11.1% |
| | | 50 eq, 60° C. $SOCl_2$ 2eq | Cl-NAHS-OMe 2.6% |
| | Reaction temperature | 3.7 eq, 0° C. $SOCl_2$ 2eq | Cl-NAHS-OMe 0% |
| | | 3.7 eq, 25° C. $SOCl_2$ 2eq | Cl-NAHS-OMe 15.6% |
| | | 3.7 eq, 40° C. $SOCl_2$ 2eq | Cl-NAHS-OMe 65.6% |
| | | 3.7 eq, 60° C. $SOCl_2$ 2eq | Cl-NAHS-OMe 88.1% |

TABLE 15

| Alcohol | Main variable | Reaction condition | Reaction result |
|---|---|---|---|
| Ethanol | Ethanol equivalent | 1 eq, 60° C. $SOCl_2$ 2eq | Cl-NAHS-Oet 22.8% |
| | | 3 eq, 60° C. $SOCl_2$ 2eq | Cl-NAHS-Oet 78.9% |
| | | 3.7 eq, 60° C. $SOCl_2$ 2eq | Cl-NAHS-Oet 87.5% |
| | | 10 eq, 60° C. $SOCl_2$ 2eq | Cl-NAHS-Oet 19.5% |
| | | 50 eq, 60° C. $SOCl_2$ 2eq | Cl-NAHS-Oet 1.5% |
| | Reaction temperature | 3.7 eq, 0° C. $SOCl_2$ 2eq | Cl-NAHS-Oet 0% |
| | | 3.7 eq, 25° C. $SOCl_2$ 2eq | Cl-NAHS-Oet 18.6% |
| | | 3.7 eq, 40° C. $SOCl_2$ 2eq | Cl-NAHS-Oet 61.3% |
| | | 3.7 eq, 60° C. $SOCl_2$ 2eq | Cl-NAHS-Oet 87.5% |

TABLE 16

| Alcohol | Main variable | Reaction condition | Reaction result |
|---|---|---|---|
| Isopropanol | Isopropanol equivalent | 1 eq, 60° C. $SOCl_2$ 2eq | Cl-NAHS-OiPr 25.8% |
| | | 3 eq, 60° C. $SOCl_2$ 2eq | Cl-NAHS-OiPr 68.5% |
| | | 3.7 eq, 60° C. $SOCl_2$ 2eq | Cl-NAHS-OiPr 70.3% |
| | | 10 eq, 60° C. $SOCl_2$ 2eq | Cl-NAHS-OiPr 14.7% |
| | | 50 eq, 60° C. $SOCl_2$ 2eq | Cl-NAHS-OiPr 0% |
| | Reaction temperature | 3.7 eq, 0° C. $SOCl_2$ 2eq | Cl-NAHS-OiPr 0% |
| | | 3.7 eq, 25° C. $SOCl_2$ 2eq | Cl-NAHS-OiPr 22.3% |
| | | 3.7 eq, 40° C. $SOCl_2$ 2eq | Cl-NAHS-OiPr 54.9% |
| | | 3.7 eq, 60° C. $SOCl_2$ 2eq | Cl-NAHS-OiPr 70.3% |

TABLE 17

| Alcohol | Main variable | Reaction condition | Reaction result |
|---|---|---|---|
| Butanol | Butanol equivalent | 1 eq, 60° C. $SOCl_2$ 2eq | Cl-NAHS-OBu 22.7% |
| | | 3 eq, 60° C. $SOCl_2$ 2eq | Cl-NAHS-OBu 44.5% |
| | | 3.7 eq, 60° C. $SOCl_2$ 2eq | Cl-NAHS-OBu 58.3% |
| | | 10 eq, 60° C. $SOCl_2$ 2eq | Cl-NAHS-OBu 5.8% |
| | | 50 eq, 60° C. $SOCl_2$ 2eq | Cl-NAHS-OBu 0% |
| | Reaction temperature | 3.7 eq, 0° C. $SOCl_2$ 2eq | Cl-NAHS-OBu 0% |
| | | 3.7 eq, 25° C. $SOCl_2$ 2eq | Cl-NAHS-OBu 6.4% |
| | | 3.7 eq, 40° C. $SOCl_2$ 2eq | Cl-NAHS-OBu 25.6% |
| | | 3.7 eq, 60° C. $SOCl_2$ 2eq | Cl-NAHS-OBu 58.3% |

As shown in Tables 14 to 17, it was confirmed that it is possible to prepare a third intermediate compound represented by Chemical Formula 2 from the first intermediate compound represented by Chemical Formula 2 using methanol, ethanol, isopropanol, and butanol.

The invention claimed is:

1. A method for preparing a compound of Chemical Formula 2, the method comprising a step a of preparing a compound of the following Chemical Formula 2 from a compound of the following Chemical Formula 1,
  wherein the step a comprises
  (i) a step b of preparing a compound of the following Chemical Formula 3 by reacting the compound of Chemical Formula 1 with a first base catalyst, or
  (ii) a step b-1 of preparing a compound of the following Chemical Formula 4 by reacting the compound of Chemical Formula 1 with a second acid catalyst, <Chemical Formula 1>

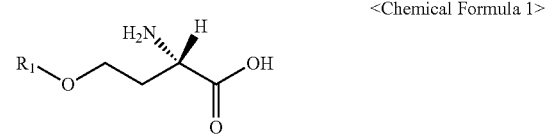

<Chemical Formula 2>

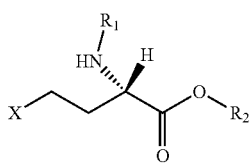

<Chemical Formula 3>

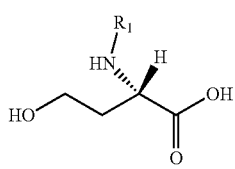

<Chemical Formula 4>

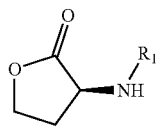

where in the above formulas, $R_1$ is $R_a$—(C=O)—, where $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_a$), where $R_b$, $R_c$ and $R_d$ independently of one another are a substituted or unsubstituted alkyl group having 1 to 6 carbon atoms or a substituted or unsubstituted aryl group having 6 to 20 carbon atoms, X is halogen, and substituents of the alkyl group, alkenyl group, alkynyl group, cycloalkyl group, aryl group, and heteroaryl group independently of one another are at least one selected from halogen, a carboxyl group (—COOH), an amino group (—NH$_2$), a nitro group (—NO$_2$), a cyano group (—CN), an alkyl group having 1 to 6 carbon atoms, an aryl group having 6 to 10 carbon atoms, and a cycloalkyl group having 3 to 10 carbon atoms.

2. The method for preparing a compound of Chemical Formula 2 according to claim 1, wherein the step a comprises a step c of preparing a compound of the following Chemical Formula 4 by reacting the compound of Chemical Formula 3 with a first acid catalyst after the step b <Chemical Formula 4>

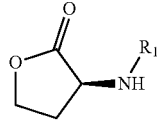

where in the above formula, $R_1$ is $R_a$—(C=O)—, where $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms.

3. The method for preparing a compound of Chemical Formula 2 according to claim 2, wherein the step a comprises a step d of preparing the compound of Chemical Formula 2 by reacting the compound of Chemical Formula 4 with a halogenating agent and at least one $R_2$—OH after the step c, wherein $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_a$), where $R_b$, $R_c$ and $R_d$ independently of one another are a substituted or unsubstituted alkyl group having 1 to 6 carbon atoms or a substituted or unsubstituted aryl group having 6 to 20 carbon atoms.

4. The method for preparing a compound of Chemical Formula 2 according to claim 1, wherein the step a comprises a step c-1 of preparing the compound of Chemical Formula 2 by reacting the compound of Chemical Formula 3 with a halogenating agent and at least one $R_2$—OH after the step b, wherein $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_a$), where $R_b$, $R_c$ and $R_d$ independently of one another are a substituted or unsubstituted alkyl group having 1 to 6 carbon atoms or a substituted or unsubstituted aryl group having 6 to 20 carbon atoms.

5. The method for preparing a compound of Chemical Formula 2 according to claim 1, wherein the step a comprises a step d-1 of preparing the compound represented by Chemical Formula 2 by reacting the compound of Chemical Formula 4 with a halogenating agent and at least one $R_2$—OH after the step b-1, wherein $R_2$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, or a substituted or unsubstituted aryl group having 6 to 20 carbon atoms, a substituted or unsubstituted heteroaryl group having 2 to 10 carbon atoms, or —Si($R_b$)($R_c$)($R_a$), where $R_b$, $R_c$ and $R_d$ independently of one another are a substituted or unsubstituted alkyl group having 1 to 6 carbon atoms or a substituted or unsubstituted aryl group having 6 to 20 carbon atoms.

6. The method for preparing a compound of Chemical Formula 2 according to claim 1, wherein the $R_1$ is acetyl or succinyl, and the $R_2$ is any one selected from the group consisting of methyl, ethyl, propyl, butyl, pentyl, hexyl, benzyl, phenyl and naphthyl.

7. The method for preparing a compound of Chemical Formula 2 according to claim 1, wherein the compound of Chemical Formula 1 is prepared from a fermentation liquid containing the compound of Chemical Formula 1.

8. The method for preparing a compound of Chemical Formula 2 according to claim 1, wherein the first base catalyst includes at least one selected from the group consisting of $NH_3$, KOH, NaOH, $CaSO_4$, LiOH, NaH, KH, $NaOCH_3$, $NaOCH_2CH_3$, $NaOC(CH_3)_3$, $KOC(CH_3)_3$, $K_2CO_3$, $Na_2CO_3$, 1,8-diazabicyclo[5.4.0]undeca-7-ene (DBU), 1,5-diazabicyclo[4.3.0]nona-5-ene (DBN), tri($C_1$-$C_4$ alkyl)amine, pyridine and n-butyllithium.

9. The method for preparing a compound of Chemical Formula 2 according to claim 1, wherein the step b is carried out at pH of 9 to 14.

10. The method for preparing a compound of Chemical Formula 2 according to claim 2, wherein the first acid catalyst includes at least one selected from the group consisting of $CH_3COOH$, HCl, $H_2SO_4$, HBr and HI.

11. The method for preparing a compound of Chemical Formula 2 according to claim 2, wherein a content of the first acid catalyst is 0.1 to 100 equivalents based on 1 equivalent of the compound of Chemical Formula 3.

12. The method for preparing a compound of Chemical Formula 2 according to claim 2, wherein the step c is carried out at a temperature of 20 to 150° C. for a reaction time of 0.1 to 20 hours.

13. The method for preparing a compound of Chemical Formula 2 according to claim 3, wherein the halogenating agent includes at least one selected from the group consisting of HCl, HBr, HI, phosgene, $SOCl_2$, oxalyl chloride, triethylsilane+ $(CH_2CH_3)_3SiH$)+ palladium chloride ($PdCl_2$)+methyl iodide ($CH_3O$), $POCl_3$, $PCl_3$, $PCl_5$, $PBr_3$, $PI_3$, $H_2SO_4$+KBr, P+$Cl_2$, P+$Br_2$, P+$I_2$, $TiCl_4$, $ZnCl_2$ and $BBr_3$.

14. The method for preparing a compound of Chemical Formula 2 according to claim 3, wherein the $R_2$—OH includes at least one selected from the group consisting of methanol, ethanol, n-propanol, iso-propanol, butanol, pentanol, hexanol, benzyl alcohol, phenol and naphthol.

15. The method for preparing a compound of Chemical Formula 2 according to claim 4, wherein the step c-1 is carried out at a reaction temperature of 20 to 120° C. for a reaction time of 0.1 to 30 hours.

16. The method for preparing a compound of Chemical Formula 2 according to claim 5, wherein the step d-1 is carried out at a reaction temperature of 20 to 100° C. for a reaction time of 0.1 to 30 hours.

17. The method for preparing a compound of Chemical Formula 2 according to claim 3, wherein a content of the halogenating agent is 1 to 10 equivalents based on 1 equivalent of the compound of Chemical Formula 3 or the compound of Chemical Formula 4, and
a content of the $R_2$—OH is 1 to 60 equivalents based on 1 equivalent of the compound of Chemical Formula 3 or the compound of Chemical Formula 4.

18. The method for preparing a compound of Chemical Formula 2 according to claim 1, wherein the second acid catalyst includes at least one selected from the group consisting of acetic acid, formic acid, butyric acid, pentanoic acid, and propionic acid.

19. The method for preparing a compound of Chemical Formula 2 according to claim 1, wherein a content of the second acid catalyst is 0.1 to 20 equivalents based on 1 equivalent of the compound of Chemical Formula 1.

20. The method for preparing a compound of Chemical Formula 2 according to claim 1, wherein the step of preparing the compound of Chemical Formula 4 is carried out at a temperature of 20 to 100° C. for a reaction time of 1 to 20 hours.

21. A method for preparing L-glufosinate, the method comprising a step of preparing a compound of the following Chemical Formula 2 from a compound of the following Chemical Formula 1 by the method according to claim 1 and a step of preparing L-glufosinate from the compound of Chemical Formula 2:

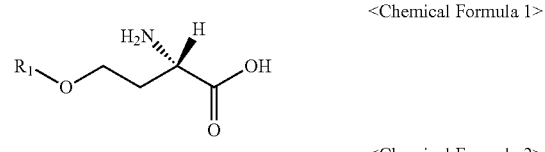

<Chemical Formula 1>

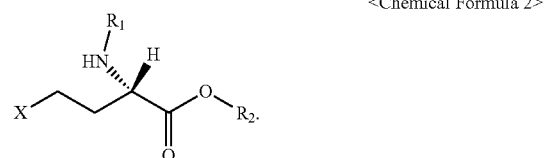

<Chemical Formula 2>

* * * * *